United States Patent
Baldwin

(10) Patent No.: US 7,469,518 B2
(45) Date of Patent: Dec. 30, 2008

(54) METHOD FOR HANDLING AND LABELING SYRINGES

(75) Inventor: Brian Eugene Baldwin, Centennial, CO (US)

(73) Assignee: Baxa Corporation, Englewood, CO (US)

( * ) Notice: Subject to any disclaimer, the term of this patent is extended or adjusted under 35 U.S.C. 154(b) by 220 days.

(21) Appl. No.: 11/427,740

(22) Filed: Jun. 29, 2006

(65) Prior Publication Data

US 2006/0260275 A1 Nov. 23, 2006

Related U.S. Application Data

(60) Division of application No. 11/361,326, filed on Feb. 24, 2006, now Pat. No. 7,207,152, which is a division of application No. 10/864,610, filed on Jun. 9, 2004, now abandoned, which is a continuation of application No. 09/928,007, filed on Aug. 10, 2001, now Pat. No. 6,813,868.

(60) Provisional application No. 60/224,136, filed on Aug. 10, 2000.

(51) Int. Cl.
*B65B 13/02* (2006.01)

(52) U.S. Cl. .......................... 53/425; 53/48.1; 53/48.7; 53/250

(58) Field of Classification Search ............ 53/411, 53/468, 425, 467, 471, 426, 473, 489; 604/197
See application file for complete search history.

(56) References Cited

U.S. PATENT DOCUMENTS

| 2,194,220 A | 3/1940 | Elder | 40/637 |
| 3,228,129 A | 1/1966 | Gwinn et al. | 40/662 |
| 3,391,694 A | 7/1968 | Spaeth | 604/189 |
| 3,597,826 A | 8/1971 | Shields | 29/208 B |
| 3,599,389 A | 8/1971 | Hartman | 53/51 |

(Continued)

FOREIGN PATENT DOCUMENTS

EP 0 935 969 A2 8/1999

(Continued)

OTHER PUBLICATIONS

FL Pharm Perm App, Jul. 2004, pp. 10 and 12.

(Continued)

*Primary Examiner*—Brian D Nash
(74) *Attorney, Agent, or Firm*—Marsh Fischmann & Breyfogle LLP

(57) ABSTRACT

An inventive method, system and apparatus are provided for syringe handling, and more particularly, for syringe labeling, filling and capping operations. To facilitate syringe handling, an inventive apparatus includes a plurality of syringe bodies interconnected in a predetermined orientation by a belt. Such belt may be of pliable construction and may define a predetermined spacing in between adjacent ones of the syringe bodies, such predetermined spacing corresponding with a distance between holders provided in a handling apparatus. The syringe handling apparatus may provide for the placement of contents-related information on belt segments between adjacent syringe bodies and for separating the belt segments, wherein a flap is left interconnected to each syringe body. The syringe handling apparatus may alternatively or also provide for automated filling of the syringe bodies wherein cap removal, filling and cap replacement operations are completed free from manual handling.

26 Claims, 22 Drawing Sheets

U.S. PATENT DOCUMENTS

| | | | |
|---|---|---|---|
| 3,611,656 A | 10/1971 | Chidsey | 53/398 |
| 3,634,175 A | 1/1972 | Delle Vite | 156/568 |
| 3,650,773 A | 3/1972 | Bush et al. | 99/171 R |
| 3,653,176 A | 4/1972 | Gess | 53/64 |
| 3,662,517 A | 5/1972 | Tascher et al. | 53/282 |
| 3,683,483 A | 8/1972 | Klettke | 29/208 B |
| 3,686,820 A | 8/1972 | Zenger et al. | 53/3 |
| 3,698,383 A | 10/1972 | Baucom | 128/2 |
| 3,708,945 A | 1/1973 | Klettke | 53/22 R |
| 3,713,771 A | 1/1973 | Taylor et al. | 23/230 R |
| 3,729,892 A | 5/1973 | Aslund et al. | 53/23 |
| 3,770,026 A | 11/1973 | Isenberg | 141/2 |
| 3,791,009 A | 2/1974 | Gess | 29/208 B |
| 3,801,291 A | 4/1974 | Shields | 29/208 B |
| 3,802,987 A | 4/1974 | Noll | 156/296 |
| 3,807,119 A | 4/1974 | Shields | 53/22 R |
| 3,823,818 A | 7/1974 | Shaw | 206/390 |
| 3,835,897 A | 9/1974 | Gess | 141/98 |
| 3,878,967 A | 4/1975 | Joslin et al. | 221/88 |
| 3,885,562 A | 5/1975 | Lampkin | 128/218 R |
| 3,955,020 A | 5/1976 | Cavanagh et al. | 428/35 |
| 3,994,085 A | 11/1976 | Groselak et al. | 40/21 R |
| 4,115,939 A | 9/1978 | Marks | 40/310 |
| 4,118,914 A | 10/1978 | Shields | 53/282 |
| 4,135,561 A | 1/1979 | Senelonge | 141/234 |
| 4,142,633 A | 3/1979 | Raghavachari et al. | 206/366 |
| 4,167,229 A | 9/1979 | Keusch et al. | 206/343 |
| 4,271,587 A | 6/1981 | Shields | 29/809 |
| 4,278,167 A | 7/1981 | van Rossem | 206/45.34 |
| 4,312,523 A | 1/1982 | Haines | 283/18 |
| 4,372,681 A | 2/1983 | Sallenbach | 356/72 |
| 4,436,478 A | 3/1984 | Allen et al. | 414/752 |
| 4,456,115 A | 6/1984 | McKnight et al. | 198/377 |
| 4,501,306 A | 2/1985 | Chu et al. | 141/94 |
| 4,579,759 A | 4/1986 | Breuers | 428/36 |
| 4,628,969 A | 12/1986 | Jurgens, Jr. et al. | 141/1 |
| 4,658,974 A | 4/1987 | Fujita et al. | 215/12 R |
| 4,674,652 A | 6/1987 | Aten et al. | 221/3 |
| 4,718,463 A | 1/1988 | Jurgens, Jr. et al. | 141/11 |
| 4,763,930 A | 8/1988 | Matney | 283/81 |
| 4,815,625 A | 3/1989 | Filhol et al. | 220/23.4 |
| 4,842,028 A | 6/1989 | Kaufman et al. | 141/114 |
| 4,865,592 A | 9/1989 | Rycroft | 604/197 |
| 4,884,827 A | 12/1989 | Kelley | 283/81 |
| 4,907,394 A | 3/1990 | Tschepke et al. | 53/412 |
| 4,921,277 A | 5/1990 | McDonough | 283/81 |
| 4,945,707 A | 8/1990 | Cosmo | 53/399 |
| 5,024,347 A | 6/1991 | Baldwin | 222/1 |
| 5,071,168 A | 12/1991 | Shamos | 283/117 |
| 5,157,894 A | 10/1992 | Mini et al. | 53/148 |
| 5,282,348 A | 2/1994 | Dampier et al. | 53/398 |
| 5,283,093 A | 2/1994 | All | 428/41 |
| 5,321,933 A | 6/1994 | Seifert et al. | 53/415 |
| 5,356,393 A | 10/1994 | Haber et al. | 604/222 |
| 5,366,249 A | 11/1994 | Diemert | 283/80 |
| 5,373,684 A | 12/1994 | Vacca | 53/425 |
| 5,390,469 A | 2/1995 | Shimizu et al. | 53/53 |
| 5,410,827 A | 5/1995 | Smith | 40/1.5 |
| 5,468,022 A | 11/1995 | Linder et al. | 283/72 |
| 5,573,042 A | 11/1996 | De Haen | 141/2 |
| 5,597,530 A | 1/1997 | Smith et al. | 422/28 |
| 5,609,712 A | 3/1997 | Takumi | 156/298 |
| 5,651,775 A | 7/1997 | Walker et al. | 604/207 |
| 5,692,640 A | 12/1997 | Caulfield et al. | 221/70 |
| 5,765,345 A | 6/1998 | Svec | 53/453 |
| 5,884,457 A | 3/1999 | Ortiz et al. | 53/468 |
| 5,954,700 A | 9/1999 | Kovelman | 604/232 |
| 5,984,901 A | 11/1999 | Sudo et al. | 604/227 |
| 6,012,595 A | 1/2000 | Thilly | 211/60.1 |
| 6,065,270 A | 5/2000 | Reinhard et al. | 53/426 |
| 6,070,761 A | 6/2000 | Bloom et al. | 222/81 |
| 6,141,939 A | 11/2000 | Pedrotti et al. | 53/48.1 |
| 6,164,044 A | 12/2000 | Porfano et al. | 53/471 |
| 6,189,195 B1 | 2/2001 | Reilly et al. | 29/434 |
| 6,263,641 B1 | 7/2001 | Odell et al. | 53/425 |
| 6,685,678 B2 | 2/2004 | Evans et al. | 604/207 |
| 6,722,404 B2 | 4/2004 | Osborne | 141/133 |
| 6,742,246 B2 | 6/2004 | Stroup | 29/823 |
| 6,813,868 B2 | 11/2004 | Baldwin et al. | |
| 6,915,619 B2 | 7/2005 | Baldwin | |
| 6,957,522 B2 | 10/2005 | Baldwin et al. | |
| 6,976,349 B2 | 12/2005 | Baldwin et al. | |
| 7,207,152 B2 | 4/2007 | Baldwin | |
| 7,392,638 B2 | 7/2008 | Baldwin et al. | |
| 2006/0260276 A1 | 11/2006 | Baldwin | |

FOREIGN PATENT DOCUMENTS

WO     WO 98/32690     7/1998

OTHER PUBLICATIONS

Pharm Newsletter, Spring 99, vol. 11, No. 1, pp. 1 and 13, w/notations by 3rd party reexam requester.

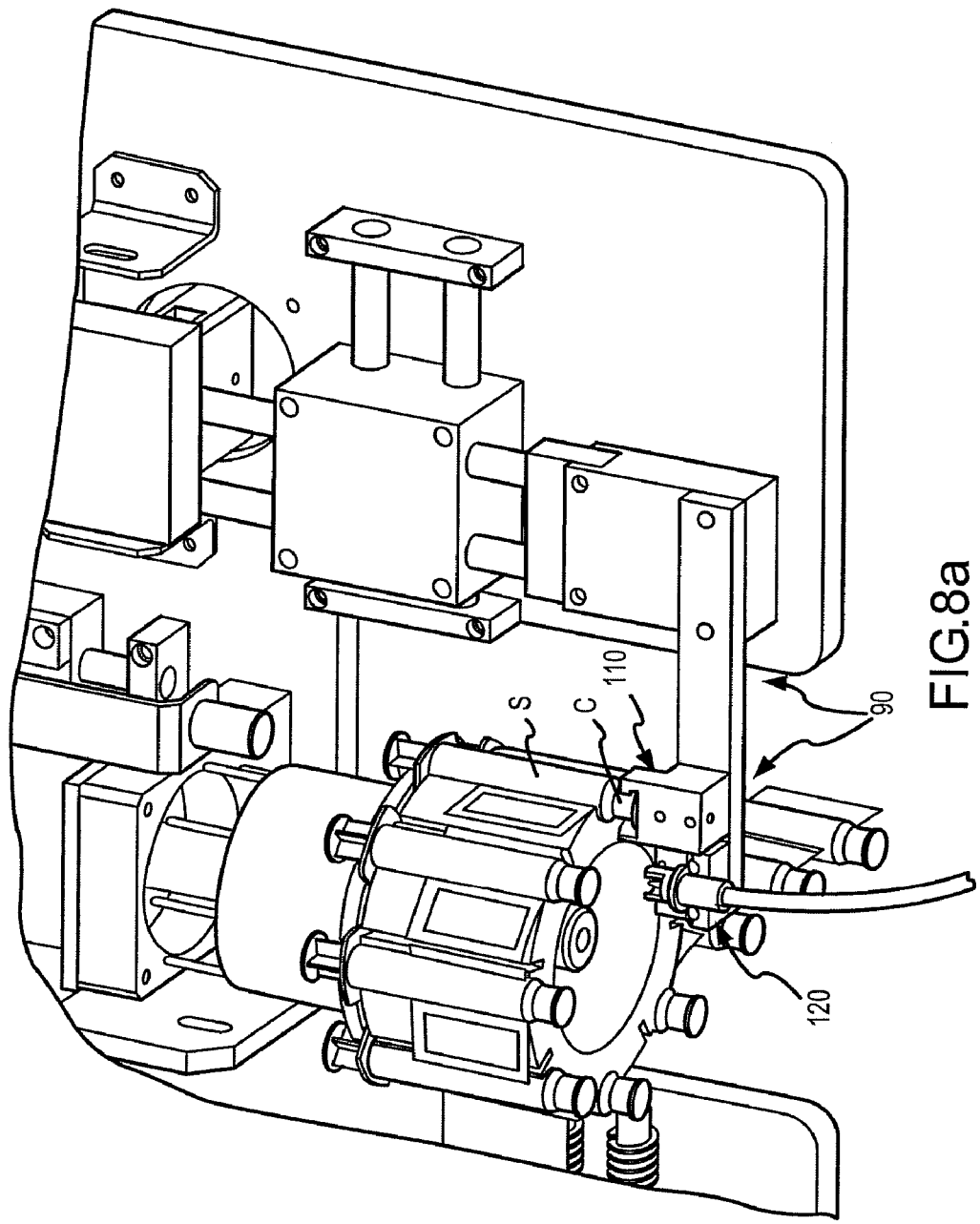

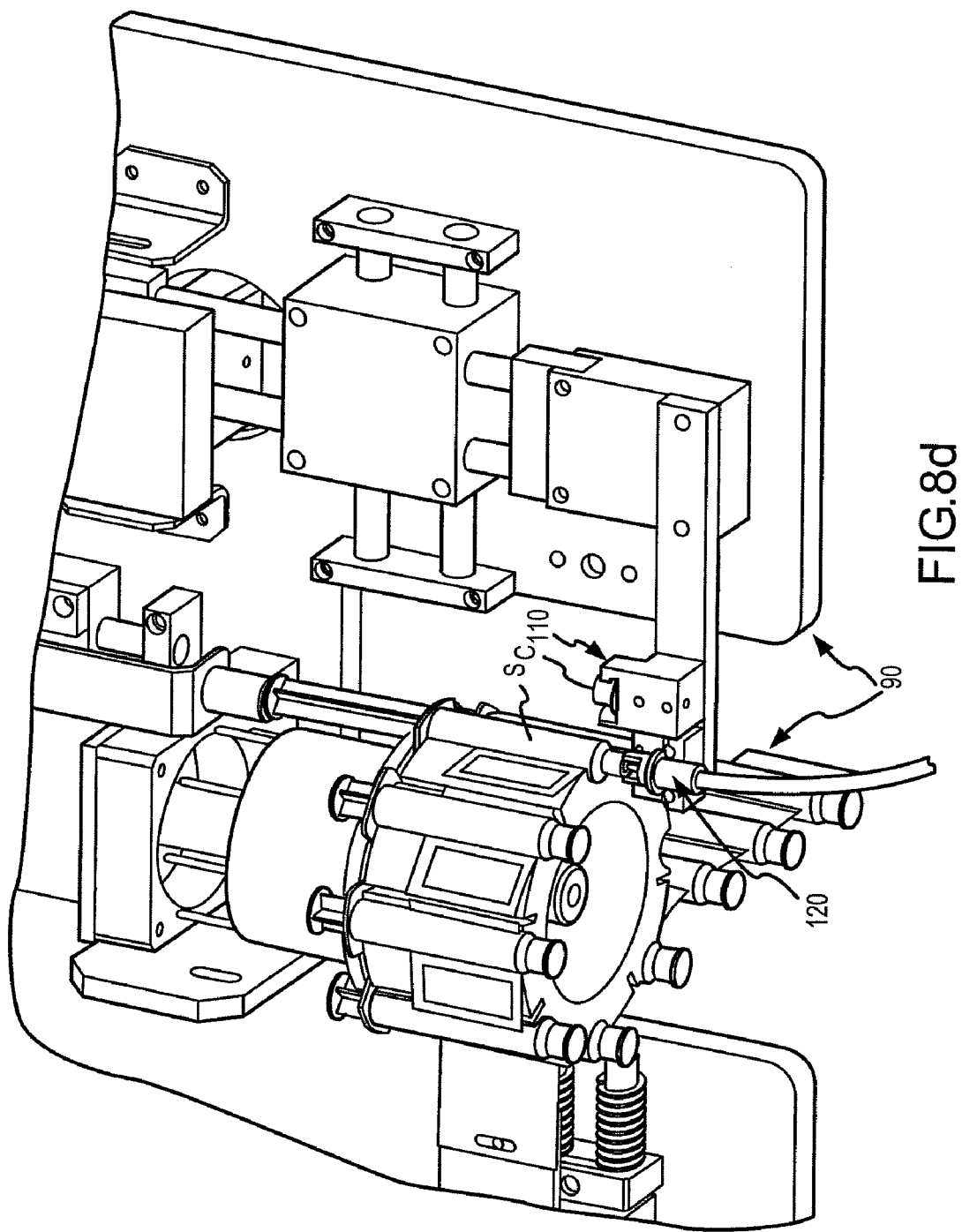

METHOD FOR HANDLING AND LABELING SYRINGES

RELATED APPLICATIONS

This application is a divisional application of U.S. patent application Ser. No. 11/361,326 filed Feb. 24, 2006, now U.S. Pat. No. 7,207,152, which is a divisional application of U.S. patent application Ser. No. 10/864,610 filed Jun. 9, 2004, now abandoned, which is a continuation of U.S. patent application Ser. No. 09/928,007 filed Aug. 10, 2001, now U.S. Pat. No. 6,813,868, which claims priority under 35 U.S.C. § 119 to U.S. Provisional Patent Application Ser. No. 60/224,136, filed Aug. 10, 2000.

FIELD OF THE INVENTION

The present invention generally relates to the handling of syringes, and is particularly apt for use in automated syringe handling operations, such as syringe filling, labeling and capping operations.

BACKGROUND OF THE INVENTION

Each year countless syringes are used throughout the world by the healthcare industry for the administration of liquid medications to humans and animals with hypodermic needles or infusion catheters, as well as for delivery of oral and topical medications. Some medications provided by pharmaceutical manufacturers are prepared, stored, and shipped as powders, crystals, or some other solid form due to the lack of stability in solution. These medications are then reconstituted with liquid, such as water or some other suitable liquid solvent. For one or several administrations of a medication, the manual filling of the syringes with reconstituted liquid medication is a small chore. However, larger health care institutions often administer medications in syringes to hundreds of patients per day, thus requiring the rather large chore of filling hundreds of syringes with medications and labeling each filled syringe to show the contents, strength, and fill dates, usually under the direction of a qualified pharmacist. Healthcare providers have found that preparing (e.g. filling and labeling) the quantities of syringes needed has many efficiencies and other advantages when it is done in batches.

In the later regard, batch preparation may be particularly preferred for syringes carrying medications that are not stable in liquid form and are therefore frozen after preparation to maintain acceptable stability. Further, the task of maintaining sterility in the transfer of liquid from containers provided by pharmaceutical manufacturers to pre-sterilized syringes may be enhanced by batch completion in controlled environments. Also, safety and overall reliability may improve when syringes are prepared in batches by pharmacy personnel or others who are dedicated to and well-trained for the task.

Currently, syringe preparation typically entails a number of separate operations with individual syringe handling. For example, systems used today fill syringes with dispensing pumps that are capable of delivering exact quantities of fluids but that require individual handling of each syringe. Peristaltic pumps that can be accurately calibrated, such as that described in U.S. Pat. No. 5,024,347, are often used. In such arrangements, the syringe caps are packaged so that sterility can be maintained in the capping procedure. The caps are located in trays where each cap is positioned so that the person doing the filling can manually place the tip of the syringe into the cap without touching or holding the cap. Labeling of the syringes has been done using a label dispenser similar to those used for applying pricing labels to grocery or other similar products.

With smaller syringes there are sometimes problems with getting sufficient label information on the syringe without covering over the syringe graduations or blocking the view of the medication. To overcome this, the labels are often applied by hand with the label wrapped around the syringe with most of the label extending from the syringe to form a flag.

Silicone lubricants are used in syringe manufacturing to provide lubrication for lowering the frictional force in movement of the syringe plunger. These silicone lubricants have a characteristic of migrating over all surfaces. Often, this migration causes difficulties in getting pressure sensitive labels to stay in place. This has caused users to use a clear plastic tape to wrap completely around the syringe and the label.

Efforts to automate hospital or clinic-based syringe preparation have been made, but most systems have automated only portions of the process and still require human intervention during critical stages of the process. In one such system, caps are pre-positioned in a cartridge holder. The syringes are also provided in a cartridge where each syringe is oriented. The machine to perform the filling and capping function requires an operator to load the cartridges of caps and syringes. The filling is done with a calibrated peristaltic pump. The machine fills each syringe and places a cap. The labeling is done separately by a labeling machine that is commercially available.

SUMMARY OF THE INVENTION

In view of the foregoing, a broad objective of the present invention is to provide a method, system and apparatus for enhanced syringe handling. A closely related objective is to facilitate automated syringe handling for various operations, such as syringe filling, labeling and capping.

Another objective of the present invention is to provide a syringe handling approach that facilitates the maintenance of sterility.

An additional objective of the present invention is to provide an improved syringe filling and capping approach.

Yet another objective of the present invention is to provide an improved approach for syringe labeling.

In addressing one or more of the above objectives, the present inventors have recognized that significant benefits may be realized by interconnecting multiple syringe bodies to facilitate handling of the same. More particularly, such interconnection allows multiple syringes to be commonly oriented for packaging and/or automated preparation operations.

In one aspect of the invention, an apparatus is provided that includes a plurality of syringe bodies, e.g. each comprising a barrel, and a belt fixedly connected to (e.g. adhered to or shrink-wrapped upon) each of the syringe bodies. Each syringe body may further include a plunger at least partially disposed in an open end of the barrel and a removable cap disposed on a dispensing end of the barrel. Of importance, the belt is provided to both interconnect the plurality of syringe bodies and position the same in a predetermined orientation.

In the later regard, and by way of primary example, the dispensing ends of the syringe body barrels may be oriented to extend in a common direction. In addition, the barrels of adjacent ones of the plurality of syringe bodies may be disposed in side-by-side, series relation. Further, the belt may be provided to define a predetermined spacing between adjacent ones of the syringe bodies, such spacing preferably being equidistance throughout a given assembly to accommodate ready positioning in holders adapted for automated operations, as will be further described.

To facilitate handling, production and packaging, the belt may be of a pliable construction. Further, the belt may be advantageously constructed for ready separation in automated labeling operations, as described hereinbelow. In this regard, it is advantageous for the belt to be of a predetermined length between adjacent ones of the plurality of syringe bodies, such predetermined length defining belt segments that are sufficient for the placement of contents information thereupon(e.g. via the application of a label thereto or direct printing thereupon).

Preferably, the belt is interconnected to each of the syringe body barrels. In this regard, the barrels maybe of a common length, wherein the belt is fixedly connected to the barrels along a common portion of the length of each. In addition, the belt may advantageously be of a width that exceeds a majority of a length of each of the barrels. Further, the belt may comprise a first portion that extends between adjacent ones of the plurality of syringe bodies, and a second portion that extends about at least a portion of each of the syringe body barrels. Preferably, the second portion adhesively engages the syringe body barrels and may be substantially transparent to facilitate observation of the volumetric contents within and markings on the syringe barrels.

In one approach, the belt may be defined by opposing layers adjoined in face-to-face relation between adjacent ones of the plurality of syringe bodies and wrapped about opposing sides of the barrels of each of the syringe bodies. At least one of the opposing layers may be substantially transparent to allow for visual determination of volumetric contents and amount. As may be appreciated, a clear pliable plastic material may be utilized for easy and low-cost construction of the belt.

As noted, each syringe body of the inventive apparatus may typically include a plunger and cap. In this regard, the barrel, inserted plunger and applied cap may preferably be assembled under low bioburden environment conditions, such as a class 100,000 or lower clean room. Further, and of importance, the plurality of interconnected syringe bodies should preferably be packaged (e.g. in a shipment container) and thereafter sterilized (e.g. via gamma radiation) to achieve terminal sterilization.

To facilitate the maintenance of a clean internal volume, yet allow for syringe filling, the caps utilized on syringe bodies should preferably engage dispensing ends of the barrels in a mating fashion. By way of primary example, each cap may include an inner member matingly positionable within or about a fluid port of the barrel dispensing end, and an outer member matingly positionable about an outer flange of the barrel dispensing end.

In another aspect of the present invention, a method is provided for producing an assembly of syringe bodies. The inventive method includes the steps of positioning a plurality of syringe bodies in a predetermined relative orientation, and disposing opposing layers of material about opposing sides of the syringe bodies and in face-to-face relation between adjacent ones of the syringe bodies. As may be appreciated, the inventive method defines an assembly comprising a belt that interconnects and orients a plurality of syringe bodies to facilitate handling as previously described.

In an additional more general aspect of the present invention, an overall method and apparatus for handling a plurality of syringe bodies is provided. Such method comprises the steps of positioning a plurality of syringe bodies in a predetermined orientation, and interconnecting a belt to each of the plurality of syringe bodies in said predetermined orientation.

The method may further comprise the step of positioning the plurality of syringe bodies into a plurality of holders for at least one production operation. To facilitate such positioning, the belt may advantageously define a predetermined spacing between adjacent ones of the syringe bodies, wherein the holders are separated by a distance that corresponds with the predetermined spacing between adjacent ones of the syringe bodies. Further, where the belt is constructed of a pliable material, the method may include the step of successively suspending, or hanging, adjacent ones of the syringe bodies so as to position the same for receipt by a holder.

Numerous automated production operations may be facilitated by the disclosed handling method, wherein the holders may be moved along a predetermined path during such operations. Of particular note, one or all of the following production operations may be automated utilizing the invention:

filling the plurality of syringe bodies with a predetermined fluid (e.g. reconstituted medication);

uncapping and/or recapping the plurality of syringe bodies in conjunction with filling;

and labeling the plurality of the syringe bodies to indicate the contents thereof.

Each of these production operations will be further described hereinbelow.

In relation to the inventive apparatus for handling a plurality of syringe bodies, it should be appreciated that it is particularly advantageous for the syringe bodies to be interconnected in series by a belt in a predetermined orientation and with a predetermined spacing therebetween. In the latter regard, the inventive apparatus may comprise a plurality of holders for holding the of syringe bodies, such holders being separated by a distance corresponding with the predetermined spacing.

The apparatus may further include a drive for moving the holders along a predetermined path. In this regard, the holders may be oriented so as to locate adjacent ones of the plurality of syringe bodies in substantial parallel relation, wherein the dispensing and opposing ends of the syringe bodies extend outwardly from and in a common orientation relative to the predetermined path. In turn, at least one workstation may be provided having a support member disposed to move towards and away from the dispensing ends of the syringe bodies. By way of primary example, such workstations may be provided for automated filling and/or automated cap removal/replacement, free from manual handling requirements.

Further, one or more workstations may be provided with a support member disposed to move towards and away from an outward facing surface of the belt at locations between adjacent ones of the syringe bodies. Such workstations may provide for automated separation of the belt between adjacent ones of the syringe bodies and/or automated printing of contents information on belt segments located between adjacent ones of the syringe bodies.

In a further aspect of the present invention a method and apparatus is provided for filling syringe bodies. In the inventive method, the filling of each syringe body entails the step of holding the syringe body in at least one holder and the further steps of removing a cap from, filling and replacing the cap back on the syringe body during the holding step. As may be appreciated, completion of the removing, filling and replacing steps while the syringe body is being held by at least one holder yields a significant handling advantage in that manual manipulation of a syringe body may be avoided.

The filling method may further include, for each syringe body, the steps of placing the cap on the dispensing end of the syringe body prior to the holding step, and packaging the syringe body in a container (e.g. for bulk shipment with other syringe bodies) and unpackaging the syringe body from the container after the placing step and prior to the holding step. Such sequencing allows for cap placement and packaging in a production location, followed by shipment to a remote location for unpackaging and completion of the filling method. Further in this regard, the method may include the important step of sterilizing syringe bodies after packaging (e.g. at the production facility prior to shipment).

Additionally, the method may comprise the step of interconnecting a belt to the plurality of syringe bodies in a predetermined orientation. Preferably, such interconnection occurs prior to the packaging and sterilization steps.

In conjunction with the removal and replacement of each of the caps, such steps may include, for each of the syringe bodies, the further steps of retainably engaging the cap in a retainer and moving at least one of the retainer and the holder to affect relative movement between the cap and the dispensing end of the syringe body. Further in this regard, such retainable engagement may be completed by moving the holder for a syringe along a predetermined path so as to insert the cap in the retainer.

In conjunction with noted filling step, the method may further provide for the interconnection of a fluid supply member with a dispensing end of the syringe body and for the flow of fluid into the syringe body through the interconnected fluid supply member. In one embodiment, such steps as well as the cap removal and cap replacement steps, may be completed with the syringe body held at a single location. In such embodiment the retainer, and fluid supply member may be interconnected for tandem forward/rearward and sideways movement. In another embodiment, the cap removal and cap replacement steps may be completed with a syringe body held at a first location, while the filling step may be completed at a second location. Such an approach only requires forward/rearward tandem movement of the retainer and fluid supply member.

Of note, the inventive filling method and apparatus may also provide for sensing of the position of a syringe body plunger during fluid filling. In this regard, optical sensing, pressure sensing or the like may be utilized, wherein a sense signal may be provided that reflects the fluid volume within a syringe as it is filled. In turn, the sense signal may be employed to terminate the flow of fluid at a predetermined amount. In another approach, a predetermined amount of fluid may be drawn into each syringe body via controlled retraction of the associated plunger.

As may be appreciated, the inventive apparatus for filling a plurality of syringe bodies may include at least one, and preferably a plurality of holders for holding a plurality of syringe bodies in a predetermined orientation. Further, the apparatus may include a retainer for retainably engaging the cap of a syringe body, wherein the cap may be selectively removed and replaced by the retainer. Additionally, the apparatus may include a fluid supply member disposed for selective fluid interconnection with a dispensing end of the syringe body.

To facilitate automated operations, the inventive apparatus may further comprise a driven support member for moving the holder(s) along a predetermined path. Additionally, one or more driven support members may be provided for moving the retainer towards/away from the dispensing end(s) of each syringe body and/or for moving the fluid supply member towards and away from the dispensing end(s) of each syringe body.

In yet additional aspect of the present invention, an inventive method and apparatus are provided for labeling a plurality of syringe bodies. The inventive method includes the steps of interconnecting a belt to a plurality of syringe bodies in a predetermined orientation, and placing contents-related information on belt segments interconnected to each of the syringe bodies. The method further includes the step of separating the belt between each of said plurality of syringe bodies to define an interconnected flap (e.g. corresponding with the belt segments) on each of the syringe bodies.

In conjunction with the inventive labeling method, the separating step may provide for severing, or cutting the belt between adjacent ones of the plurality of syringe bodies. Alternatively, the separating step may entail relative displacement of adjacent ones of the syringe bodies so as to achieve separation along perforation lines or the like.

With respect to the step of placing contents-related information on each given belt segment, such step may entail the printing of information on a label and fixation of such label to a belt segment. Alternatively, this step may simply be completed via printing of the contents-related information directly on a given belt segment.

In either case, the contents-related information may comprise one or more of the following types of information:

information regarding the fluid contained in a given syringe body;

information regarding fluid fill date for each given syringe body;

information regarding the volumetric fluid content of each given syringe body;

information comprising a product code corresponding with the contents of a given syringe body;

information regarding the lot or batch number corresponding with each given syringe body; and information regarding storage and/or handling instructions for each given syringe body.

As may be appreciated, such information may be provided in an alphanumeric or coded fashion. In the later regard, at least some of the information may be embodied in a bar code format to allow for optical scanning.

In further relation to the inventive labeling method, the interconnected syringe bodies may be packaged in a container, sterilized and unpackaged from the container prior to the separating and contents-information placement steps. As may be appreciated, such sequencing provides for the interconnection, packaging and sterilization of syringe bodies at a production location, and the unpackaging, separation and labeling of the syringe bodies at another location (e.g. at a location where the syringe bodies are filled with liquid medication).

The inventive labeling apparatus is particularly adapted for use with a plurality of syringe bodies interconnected by belt, as described above, and may include a plurality of holders and a labeling member for placing contents-related information on belt segments extending between the syringe bodies. The apparatus may further include a separation member for separating the belt between adjacent ones of the plurality of syringe bodies, wherein a different belt segment in the form of a flap is interconnected with each one of the plurality of syringe bodies. To facilitate operation of the separation member and labeling member, each of such members may be provided with driven support members that may be selectively actuated to such members towards and away from the belt segments.

As may be appreciated, various ones of the inventive aspects noted hereinabove may be combined to yield an inventive system for handling a plurality of syringe bodies, including a system that facilitates automated labeling and filling operations. The automated filling operations may further provide for automated cap removal and replacement.

These and other aspects, advantages, and novel features of the invention are set forth in part in the description that follows and will become apparent to those skilled in the art upon examination of the following description and figures or may be learned by practicing the invention.

BRIEF DESCRIPTION OF THE DRAWINGS

The accompanying drawings, which are incorporated in and form a part of the specification, illustrate embodiments of the present invention, and together with the descriptions serve to explain the principles of the invention.

FIGS. 8a-8d comprise isometric views of the syringe-filling station of the apparatus embodiment of FIG. 7, wherein a sequence of component positions are shown that correspond with and illustrate the sequential steps of cap removal, fluid filling, and cap replacement operations.

DETAILED DESCRIPTION OF THE INVENTION

Figure 1:
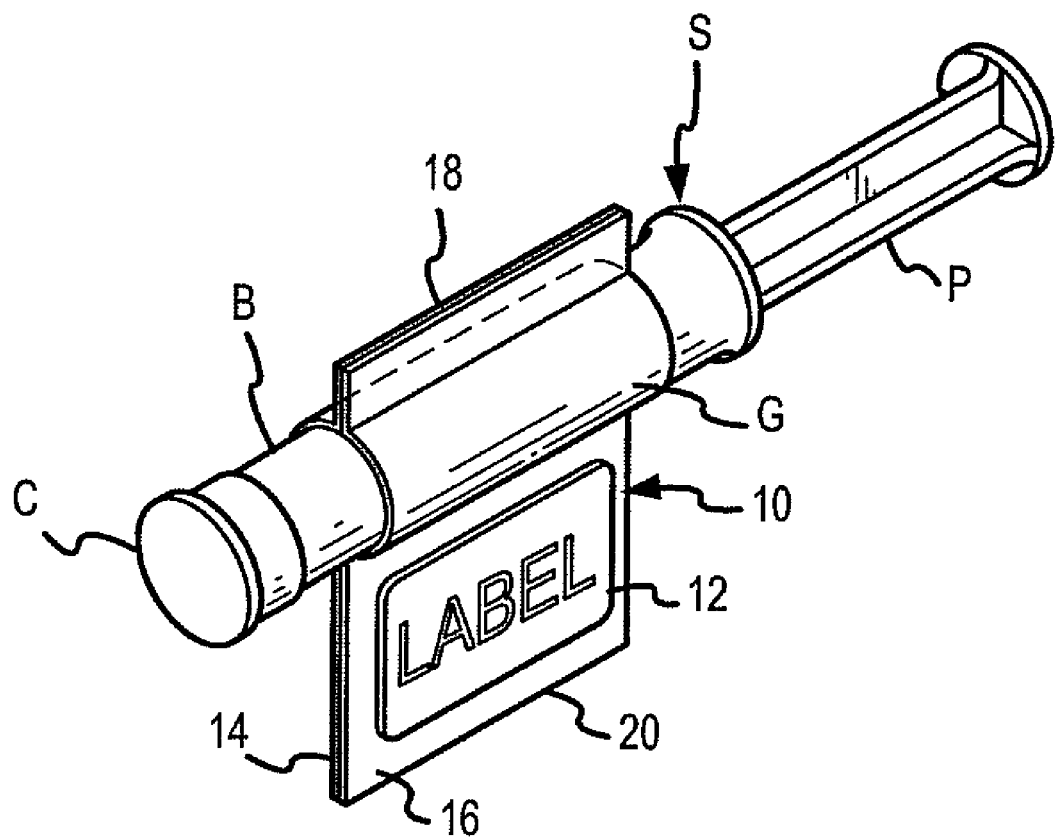
FIG. 1 is an isometric view of a labeled, filled, and capped syringe with a label substrate and label attached according to one embodiment of the present invention.

A capped syringe S that has been labeled and filled according to one embodiment of this invention is shown in FIG. 1. A cap C covers and protects the sterility of the dispensing luer tip (concealed from view in FIG. 1 by the cap C). Since the barrel B of the syringe S is full in FIG. 1, the plunger P is extended longitudinally. A flap or substrate 10 for a label 12 is provided by two strips of adhesive tape 14, 16, both of which are wrapped around and adhered to respectively opposite sides of the barrel B and adhered to each other in face-to-face relation in extensions 18, 20 of the adhesive tape 14, 16 that extend in diametrically opposite directions from the barrel B. It is preferred, but not necessary, that at least one of the adhesive tapes 14, 16 be transparent so that the graduation marks G that are on most conventional syringes as well as the plunger piston (not shown) in FIG. 1) can be seen through the adhesive tape.

In the embodiment shown in FIG. 1, the label 12 is a printed sheet that has been adhered to the panel extension 20 of the substrate 10. However, the label could also be provided in other ways according to this invention. For example, but not for limitation, the printed information could be printed directly on one or both of the adhesive tapes 14, 16. Such printing, if placed on a transparent tape 14, 16 would preferably not be enough to mask the graduation marks G. Another option could be to make one of the tapes, such as tape 14 opaque, perhaps with label information on it, but make the other tape 16 transparent so as not to mask or hide the graduation marks G. For another possibility, a sheet label similar to label 12 could be sandwiched between the two adhesive tapes 14, 16.

Figure 2:
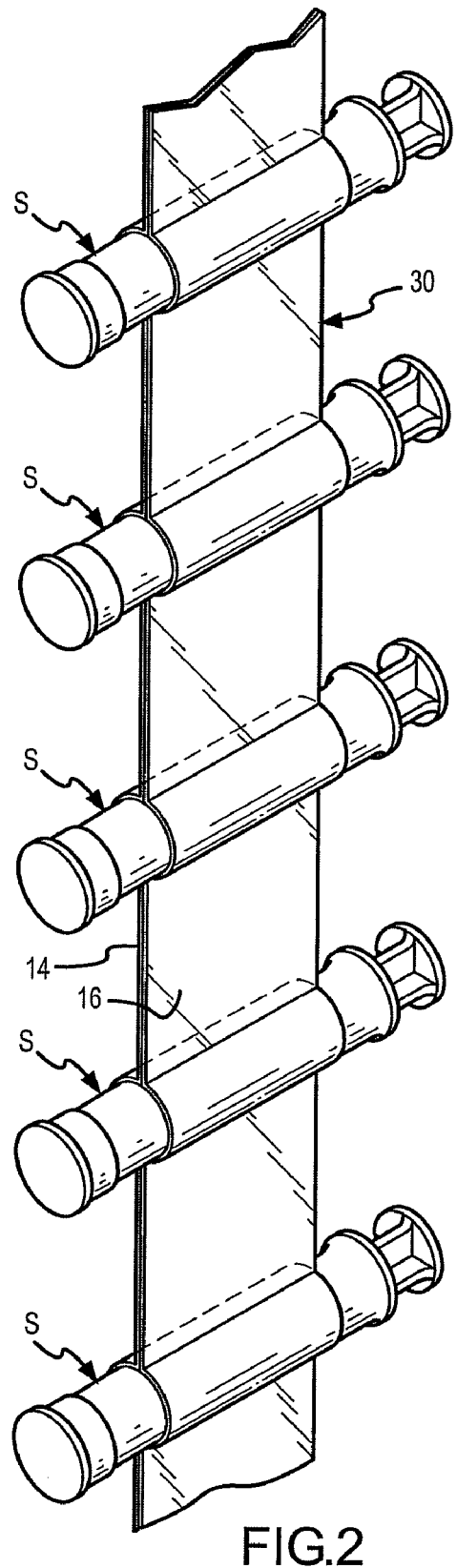
FIG. 2 is an isometric view of a plurality of sterile capped syringes mounted in a belt or band for automated labeling and/or cap removal, fluid filling, and cap replacement according to one embodiment of this invention.

As mentioned above, a significant feature of this invention is having a plurality of sterile, capped syringes S mounted in spaced apart relation to each other in a band or belt 30, as shown in FIG. 2, for handling the syringes S in automated preparation operations. For example, belt 30 may be employed for pulling the syringes S into and preferably at least partially through a labeling and/or filling apparatus and process, as will be described in more detail below. The band or belt 30 can be made with the two elongated adhesive tapes 14, 16 that were described above and which can be cut to separate the syringes S into individual syringes S with the label substrate 10 as shown in FIG. 1 and as will be described in more detail below.

Before proceeding, reference is now made to FIGS. 12a-12c and FIGS. 13a-13c which illustrate alternate embodiments of caps C employable with syringes S of the type shown in FIGS. 1 and 2. As shown, the caps C of the two embodiments each include a cylindrical outer member 500 for matingly engaging the outer flange provided at the dispensing end of the barrel B of the syringe S. In the FIG. 12a-12c embodiment, a cylindrical inner member 502 is also provided for matingly receiving the fluid port provided at the dispensing end of barrel B of syringe S. In the case of the embodiment shown in FIGS. 13a-13c a central pin-like inner member 504 is provided for mating insertion into the fluid port provided at the dispensing end of the barrel B of syringe S. Of further note, internal locating legs 506 are provided in the embodiment of FIG. 13a-13c for retentively engaging the fluid port of barrel B. As may be appreciated, the embodiments of FIG. 12a-12c and FIG. 13a-13c both provide for isolation of the contents of syringe S.

Figure 3:
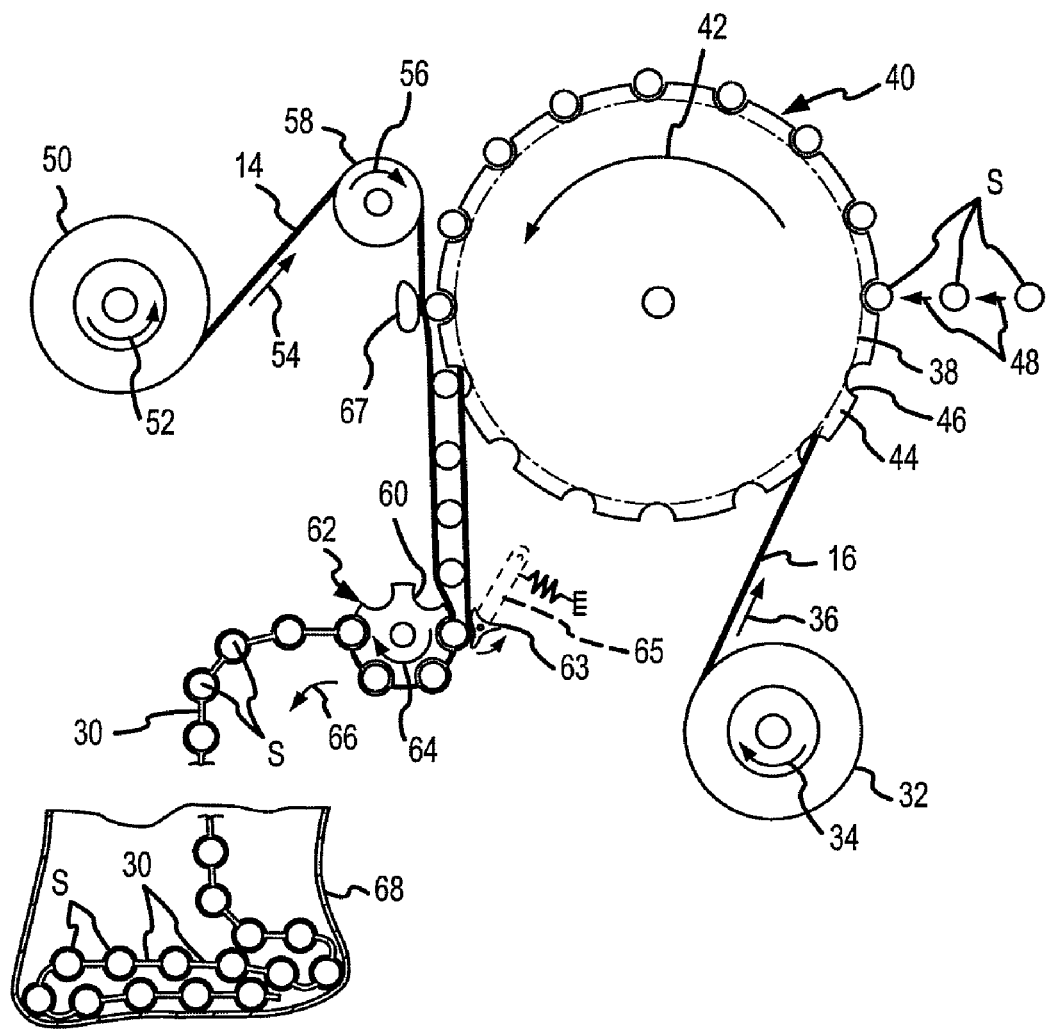
FIG. 3 is a diagrammatic elevation view of an apparatus and process for mounting syringes in a tape band or belt according to one embodiment of this invention.

There are many ways by which the plurality of syringes S can be mounted in the band or belt 30 shown in FIG. 2, and this invention is not limited to any one of such ways of doing so. However, for purposes of example, but not for limitation, one method and apparatus for mounting multiple syringes S into a band or belt 30 is shown in FIG. 3. As one tape strip, e.g., tape strip 16, is unwound from a roll 32, as indicated by arrows 34, 36, it is threaded around the periphery 38 of a syringe mounting wheel 40, which rotates as indicated by arrow 42. A pair of rims (only one rim 44 of the pair can be seen in the elevation view of FIG. 2) extend radially outward beyond each side of the periphery 38, and each of the rims 44 has a plurality of notches 46 in equal, angularly spaced relation to each other around the periphery 38. As the wheel 40 rotates, preferably capped, empty syringes S are placed serially into the notches 46, as indicated by arrows 48, where they contact the adhesive side of the tape strip 16.

As the wheel 40 rotates, as indicated by the arrow 42, it carries the syringes S in the notches 46 and in contact with the tape strip 16 to a position where the syringes S come into contact with the adhesive side of the other tape strip 14, which is simultaneously being unwound from a roll 50 as indicated by arrows 52, 54, 56. An idler wheel 58 positions the tape strip 14 in relation to the wheel 40 so that it contacts the syringes S mounted in the notches 46. Therefore, the tapes strips 14, 16 get adhered to diametrically opposite sides of the syringes S. In this regard, a contact plate 67 may also be provided to insure engagement between tape strip 14 and syringes.

As the syringes S, which are adhered to tape strips 14, 16 emerge from the wheel 40, they are captured by notches 60 in a press wheel 62 that rotates, as indicated by arrow 64, to press the tape strips 14, 16 to each other between the syringes S. Press wheel 62 may be provided for driven rotation, wherein such driven rotation effects rotation of the tape rolls 32 and 50, as well as rotation of syringe mounting wheel 40 as the tape strips 14, 16 are pulled around press wheel 62 with syringes S secured therebetween. A rotatable pressing block 63 is juxtaposed to the press wheel 62 so that the tape strips 14, 16 run between the press wheel 62 and the rotatable pressing block 63. The pressing block 63 may be configured to present a plurality of semicircular surfaces that are spaced to be in opposing relation to notches 60. Thus, the press wheel 62 and the pressing block 63 cooperate to press and adhere the tape strips 14, 16 tightly together and around the circumference of each syringe S. The pressing block 63 is preferably yieldably biased by a spring-loaded pivot arm 65 or some other bias system to press the pressing block 63 toward the press wheel 62.

After disengaging from press wheel 62, the belt 30 with the syringes S mounted therein are fed as indicated by arrow 66 into a bin or bag 68. Alternatively, the belt 30 with syringes S could be fed directly into a labeling and/or filling apparatus, which will be described below.

In general, the syringes S are positioned in the band or belt 30 in a common orientation, i.e., with luers of all the syringes S on the same side of the band 30. The notches 46 in the wheel 40 are spaced uniformly around the rim 44, so the syringes S in the resulting band 30 are spaced equidistantly apart. The caps C can be placed on the syringes S either before, while, or after the syringes S are mounted in the band 30. The band 30 of syringes S can then be fan folded or rolled and placed in the plastic bag 68, which can be closed and/or sealed to protect sterility. The package or bag 68 of banded syringes 30 can then be sterilized by any of a variety of standard sterilization processes, for example by gamma radiation. The sterilized packages 68 of sterilized, banded syringes S, usually in quantities of about 200 to 1,000 syringes S per package 68, are shipped to users, such as hospitals or other health care institutions, who will label and/or fill and re-cap the syringes S for use within an acceptable time after filling.

Figure 4:
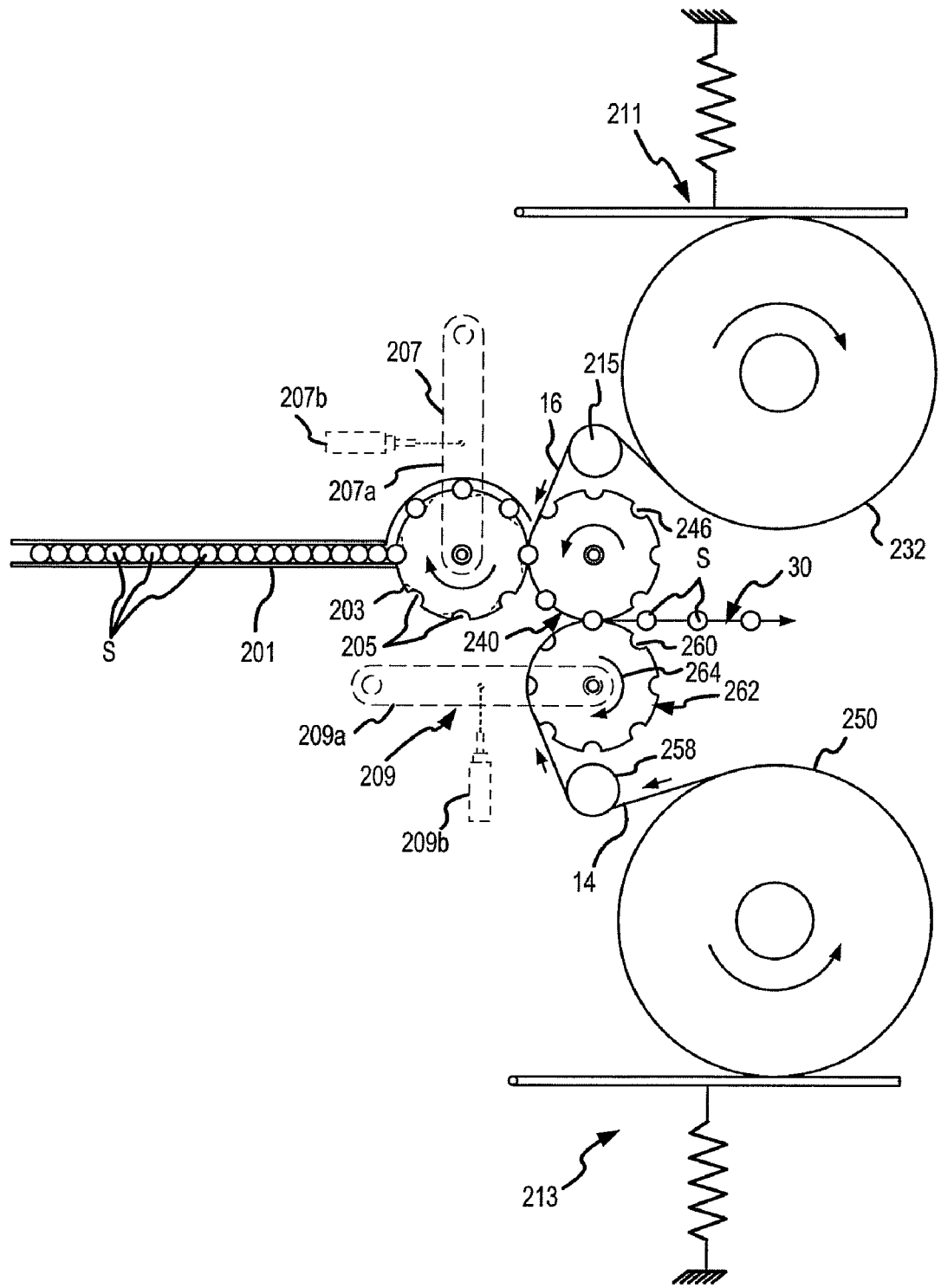
FIG. 4 is diagrammatic elevation view of an apparatus and process for mounting syringes in a tape band or belt according to another embodiment of this invention.

FIG. 4 illustrates another method and apparatus embodiment for mounting multiple syringes S into a band or belt 30. In this embodiment a syringe feed-wheel 203 is driven synchronously with tape feed wheels 240 and 262 to form a band 30 of interconnected syringes S. More particularly, tape feed wheels 240 and 262 are driven to pull adhesive tapes 16 and 14 about idler wheels 215 and 258 from tape rolls 232 and 250, respectively. Tensioning devices 211 and 213 are provided to establish a desired amount of tension along tape strips 16 and 14 as they are fed to tape feed wheels 240 and 262, respectively.

As shown by FIG. 4, a vibrating track 201 is provided to advance syringes S for sequential loading into notches 205 of the syringe feed wheel 203. In turn, the syringe feed-wheel 203 is located immediately adjacent to the tape feed-wheel 240 so that notches 246 of the tape feed-wheel and notches 205 of the syringe feed-wheel 203 are disposed in opposing relation. As such, it can be seen that tape 16 will be pressed into notches 246 on one side of syringes S to achieve conformal interconnection therewith. Further in this regard, a pneumatic position and tension control device 207 is provided to enhance the interconnection between syringes S and tape 16. Device 207 includes a mount lever arm 207a interconnected to the syringe feed-wheel 203, and a pneumatic cylinder 207b for locating the arm 207a and syringe feed-wheel 203 as appropriate so that syringes S apply a predetermined, desired amount of force against tape 16.

After interconnection of one side of syringes S to adhesive tape 16, the FIG. 4 embodiment provides for the interconnection of adhesive tape 14 to the other side of syringes S. More particularly, tape feed-wheel 262 is driven synchronously with and positioned relative to tape feed-wheel 240 so that notches 260 are in aligned relation with notches 246 to capture syringes S between adhesive tape strips 14 and 16. Concomitantly, tape 14 is pressed about the syringes S to complete band 30.

As further shown in FIG. 4, a pneumatic position and tension control device 209 is provided at the tape feed-wheel 262. Device 209 includes a mount lever arm 209a and a pneumatic cylinder 209b for locating the tape feed-wheel 262 as appropriate to establish the desired amount of force applied by syringes S to tape strip 16.

Figure 5:
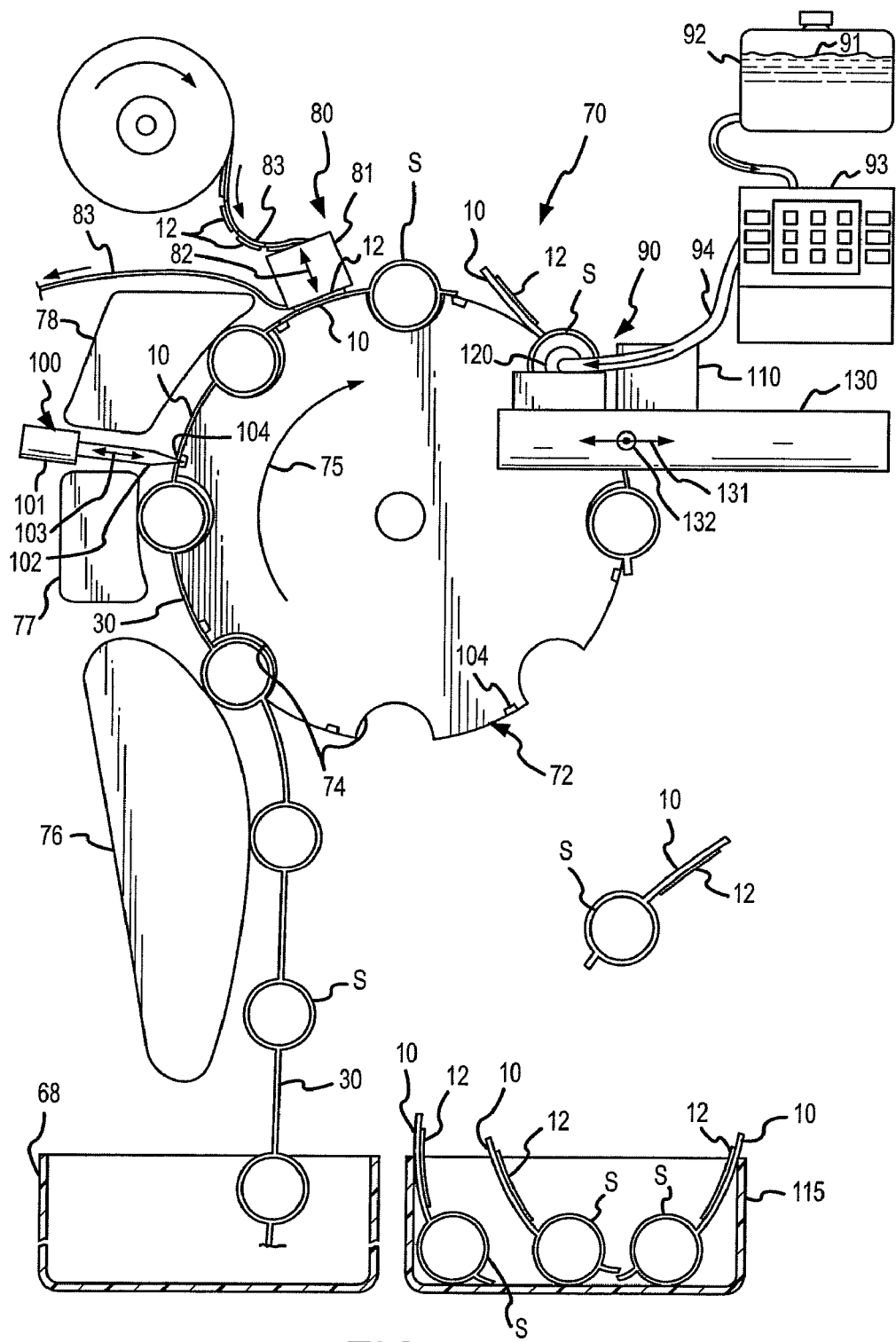
FIG. 5 is a diagrammatic elevation view of a labeling and filling apparatus of one embodiment of this invention.

Referring now to the diagrammatic elevation view of the labeling and filling apparatus 70 in FIG. 5, a band 30 of syringes S is pulled from the bag 68 by a sprocket wheel or drum 72 and rotated to positions where the band 30 is cut to form the label substrates 10 (see FIG. 1), and, if the substrates are not already labeled, to attach labels 12 to the substrates 10, and to remove the caps C, fill the syringes S with the desired medication, and replace the caps C.

In FIG. 5, if the bands 30 do not already have labels, the user will prepare a quantity of labels 12 and mount them to feed into a labeling station 80. The labels can be prepared in any suitable manner, for example, using a standard computer label printer, and the quantity of labels 12 prepared can correspond to the number of syringes S to be filled with medication that matches the labels 12. The user also prepares the liquid medication 91 in a container 92, which the user connects to a suitable fluid control system, such as conventional peristaltic pump 93 or other suitable syringe filling, fluid metering, or handling system. The medication will be conveyed via a suitable tube 94 or other conduit to the syringe filling station 90, which will be explained in more detail below. The volume of medication to be pumped into each syringe S can be set and controlled in any of a variety of ways. For example, the pump 93 can be actuated to initiate a fill and deactuated when the syringe has been filled with the desired volume of medication, as will be described in more detail below.

With continuing reference primarily to FIG. 5, the sprocket drum 72 has a plurality of notches 74 in equal, angularly-spaced relation to each other around the circumference of the drum 72. The notches 74 are large enough to receive and retain a syringe S, and they are spaced apart from each other the same distance as the spacing between the syringes S in the band 30. Therefore, when at least one of the syringes S in the band 30 is positioned in an appropriate notch 74, rotation of the drum 72, as indicated by arrow 75, will cause the band 30 to pull successive syringes S in the band 30 out of the bag 68 and into the labeling and filling apparatus 70. Suitable guides, for example, guides 76, 77, 78, can be used to hold the syringes S in the notches 74 as the drum 72 rotates and carries the syringes S through the cutting station 100, labeling station 80, and filling station 90.

It is appropriate to mention at this point that the sequential order of cutting, labeling, and filling is not critical to the invention, and these operations can be performed in any sequential order or even simultaneously, depending on how one wishes to mount the appropriate equipment, as would be within the capabilities of persons skilled in the art once the principles of this invention are understood. However, the convenient sequence of cutting, labeling, and filling will be used for purposes of this description of the invention. The drum 72 can be driven to rotate, as indicated by arrow 75, and to stop with syringes S positioned appropriately for the cutting, labeling, and filling operations at the respective stations 100, 80, 90 by any appropriate drive and control system as is well within the capability of persons skilled in the art, such as, for example, with a stepper motor (not shown) connected to appropriate motor control devices (not shown). A control panel (not shown) connected to the stepper motor can be set up for use by an operator to either jog the drum 72 through incremental steps and/or jog the cutting station 100, labeling station 80, or filling station 90 through their respective operations or to initiate continuous automatic operation.

At the cutting station 100, an actuator 101 drives a knife blade 102 as indicated by arrow 103 to cut and sever the band 30 to disconnect the syringes S from each other and to leave the resulting band segments or flaps connected to each syringe S to form individual label substrates 10 for each syringe S. The knife blade 102 is preferably serrated and a slot 104 in the drum in alignment with the knife blade 102 facilitate sure, complete cuts. Any suitable actuator 101 can be used, such as a rotary drive motor, solenoid, or the like. A sheath (not shown) can be provided to cover the blade 102 when it is not cutting. An optical or other sensor (not shown) can be positioned adjacent the drum 72 where the syringes S are first engaged by notches 74 to detect whether any syringes S have missing caps. A signal from the sensor in response to a missing cap could actuate and alarm and/or shut down the apparatus to prevent an uncapped syringe S from being labeled and filled.

For the syringe S that has advanced to the labeling station 80, a labeler device 81, moving as indicated by arrow 82, affixes a label 12 to the substrate 10. The labeler device 81 can be any of a variety of known label apparatus that transfer labels 12 from a strip 83 to an object, or it could be some other device, such as printer apparatus that prints the label directly onto the flap substrate 10, or some combination of such apparatus, as would be within the capabilities of persons skilled in the art once they understand the principles of this invention. An optical sensor (not shown) is used to detect whether a label has been affixed to the substrate 10 at the label station 80. A microprocessor (not shown) can be used to keep count of labels properly affixed and/or activate an alarm and/or shut down the apparatus 70 if a label is not detected on a substrate where a label is supposed to be affixed.

For a syringe S that has advanced to the fill station 90, the cap C (not shown in FIG. 5) is removed by a cap handling apparatus 110, then a liquid dispensing apparatus 120 is connected to the luer L (not shown in FIG. 5) of the syringe S to dispense liquid medication into the syringe S, and the pump 93 (or other suitable liquid metering or control apparatus) is actuated to move the medication 91 from the container 92 into the syringe S. When the syringe S is filled with the desired volume of fluid, as sensed, for example, by a proximity sensor that senses the corresponding desired position of the plunger P (not shown in FIG. 4) of the syringe S, the pump 93 (or other suitable liquid metering or control apparatus) is deactuated. Then, the liquid dispensing apparatus 120 is disconnected from the syringe S, and the cap handling apparatus 110 is moved into position to replace the cap C (not shown in FIG. 5) onto the luer (not shown in FIG. 4) of the syringe S. The cap handling apparatus 110 and the liquid dispensing apparatus 120 are mounted on a cammed shuttle 130, which moves laterally in two axes, as indicated by arrow 131 in the plane of the paper and by arrow 132 perpendicular to the plane of the paper, to accomplish the cap removal, fill, and cap replacement functions described above. While these functions could be performed by myriad other devices and combinations of devices, as would be within the capabilities of persons skilled in the art once they understand the principles of this invention, an example cammed shuttle 130, cap handling apparatus 110, and liquid dispensing apparatus 120 shown diagrammatically in FIG. 4 will be described in more detail below.

After the syringes S leave the fill station 90, they are allowed to drop individually out of the sprocket drum 72 and, for example, into a basket 115 or other receptacle. At this stage, the syringes S are labeled, filled, and ready for use, as shown in FIG. 1.

Referring now to FIGS. 6a, 6b, 6c, 6d, and 6e in combination with FIG. 5, the cammed shuttle 130 is driven by a motor, such as a stepper motor 133, which rotates a slotted cam lever or crank arm 134 mounted on the drive shaft 135 of the motor 133. A driver block 136 has a slide pin or a cam roll (concealed from view) extending in one direction into the slotted race groove 137 of the cam lever or crank arm 134 and another cam follow pin or cam roll 138 extending in the opposite direction into a U-shaped cam slot 139 in a stationary cam block 140. Therefore, as the stepper motor 133 rotates, for example as shown by arrow 141 in FIGS. 6b and 6c, the cam lever 134 causes the cam follower pin or cam roll 138 extending from the driver block 136 to follow the U-shaped path of the cam slot 139, which moves the two slide shafts 142, 143 extending laterally from driver block 136 as well as the connecting block 144 at the distal ends of slide shafts 142, 143 to move simultaneously in the same U-shaped motion pattern. The two slide shafts 142, 143 extend slidably through two holes 145, 146 in a pillow block 147, which is mounted slidably on two support rods 148, 149. The support rods 148, 149 are mounted in two stationary anchor blocks 150, 151 and extend slidably through two holes 152, 153 in pillow block 147, which are perpendicular to, but vertically offset from, holes 145, 146. Thus, as the stepper motor 133 drives the driver block 136 through the U-shaped pattern of cam slot 139, the pillow block 147 slides laterally on support rods 148, 149 as indicated by arrow 154, while the slide shafts 142, 143 slide longitudinally in pillow block 147 as indicated by arrow 155. As a result, the connector block 144 and cammed shuttle 130 also move both laterally and longitudinally as indicated by arrows 131, 132 in the same U-shape pattern as the U-shaped cam slot 139 to remove the cap C from the syringe S, connect the syringe S to a nozzle 121 in the liquid dispensing apparatus 120 to fill the syringe S, disconnect the nozzle 121, and replace the cap C, as will be described in more detail below. Suitable bushing or bearings can be used to enhance the sliding movement of the shafts 142, 143 and support rods 148, 149 in the pillow block 147.

Figure 6A:
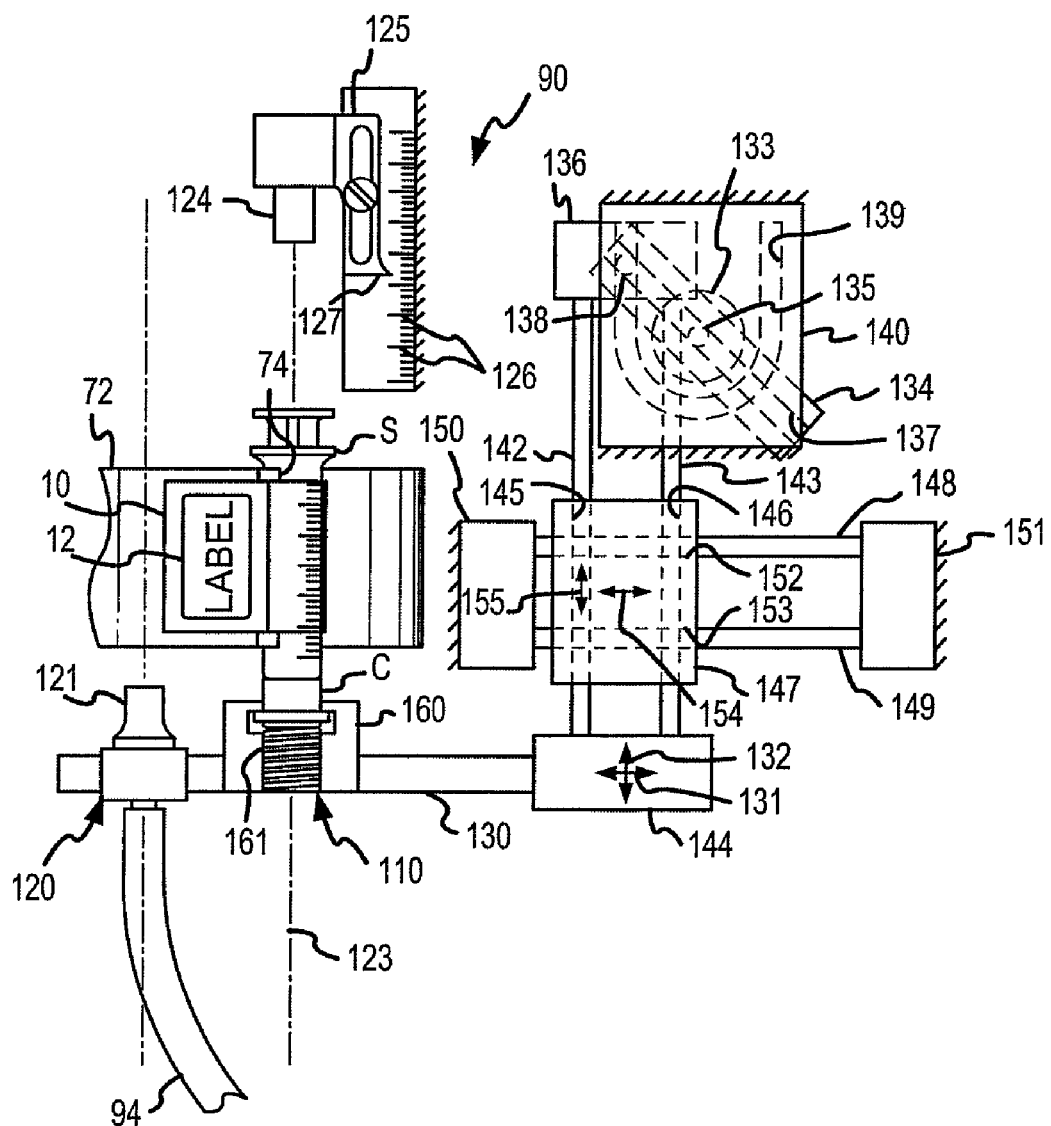
FIGS. 6a through 6e comprise diagrammatic plan views of the syringe-filling station on the apparatus embodiment of FIG. 5 wherein a sequence of component positions are shown that correspond to and illustrate sequential steps of cap removal, fluid filling, and cap replacement operation.
Figure 6B:
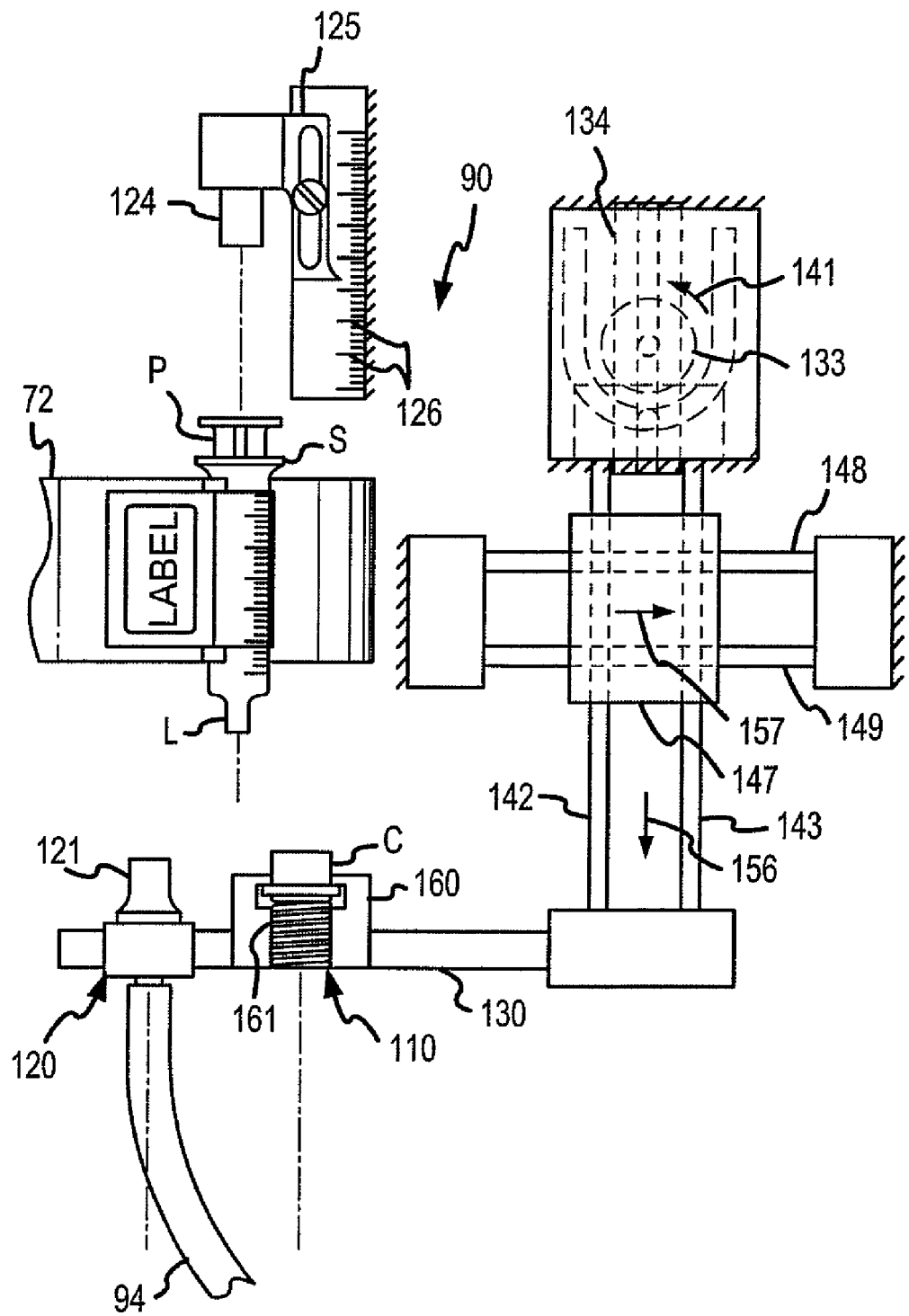

Referring now to FIG. 6a in combination with FIG. 4, the drum 72 has moved a syringe S to the filling station 90, where it stops for the cap removal, fill, and cap replacement operation. The syringe S is shown in FIG. 6a positioned in a notch 74 with a label 12 affixed to the substrate 10. As the drum 72 moved the syringe S to the position shown in FIG. 6a, the cap C was moved into a set of jaws 160, which is aligned longitudinally with the syringe S when the slotted cam lever 134 is stopped in the position shown in FIG. 6a and the drum 72 stops the syringe S in the filling station 90. A cap gripper 161, such as resilient spring steel, presses against the cap C in jaws 160 to capture and retain the cap C in the jaws 160. Again, optical sensors (not shown) or other suitable sensors and/or control devices or methods can be used to stop the drum 72 when the syringe S is positioned with the cap C captured in the jaws 160 as would be understood by persons skilled in the art once they understand the principles of this invention. Then, the motor 133 is actuated to rotate the slotted cam lever 134 as indicated by arrow 141 in FIG. 6b, which extends the slide shafts 142, 143, as indicated by arrow 156, as the pillow block 147 slides to the right on support rods 148, 149, as indicated by arrow 157. As a result, the cammed shuttle 130 moves the jaws 160 with the cap C away from the syringe S, thereby removing the cap C from the syringe S and leaving the luer L of the syringe S exposed and open, as shown in FIG. 6b. Again, the gripper 161 described above retains the cap C in the jaws 160 when the cap C is removed from the luer L.

Figure 6C:
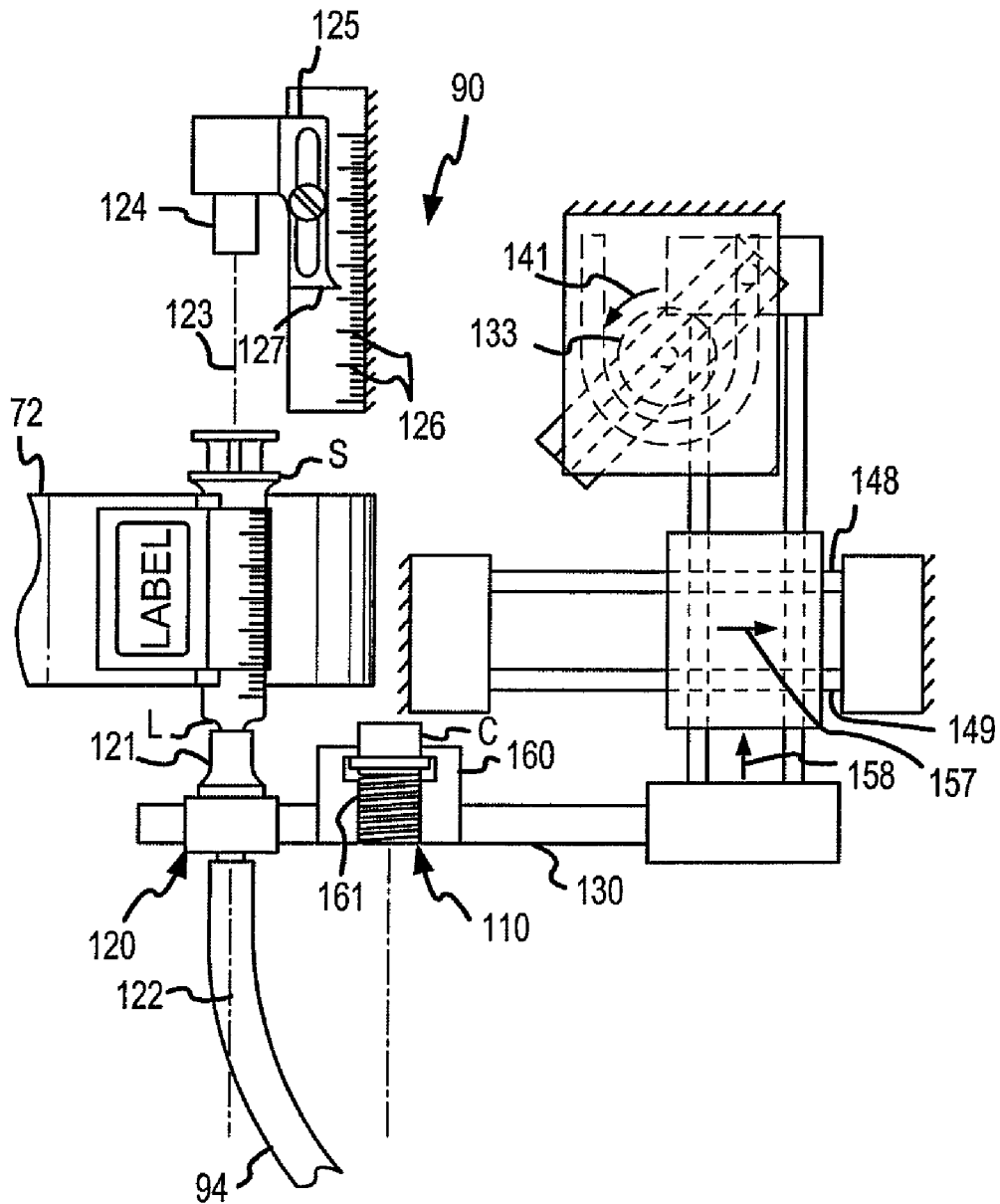

Continued rotation of the cam lever 134 as indicated by the arrow 141 in FIG. 6c translates the pillow block 147 still farther to the right on support rods 148, 149, as indicated by arrow 157 in FIG. 6c, until the longitudinal axis 122 of the fill connector or nozzle 121 aligns with the longitudinal axis 123 of syringe S, then retracts the slide shafts 142, 143, as indicated by arrow 158, to position the nozzle 121 on luer L of the syringe S. At that position of the cammed shuttle 130, the motor 133 is deactuated, so the nozzle 121 stays on the luer L while the pump 93 (FIG. 5) is actuated to pump liquid medication 91 from the container 92 to fill the syringe S. The fill connector or nozzle 121 is preferably mounted on the cammed shuttle 130 by a spring-loaded slide (not shown) or similar yieldable, resilient mounting to apply an appropriate, uniform force to the nozzle 121 as it is being forced by the cammed shuttle 130 onto the luer L of the syringe S. This motion to remove the cap C and place the fill connector or nozzle 121 on the syringe S can be accomplished in approximately 250 milliseconds with this mechanism. The U-shaped cam slot 139 provides a straight, longitudinal pull of the cap C in alignment with the longitudinal axis 123 of the syringe S and a corresponding straight, longitudinal push to attach the nozzle 121 to the luer L.

Figure 6D:
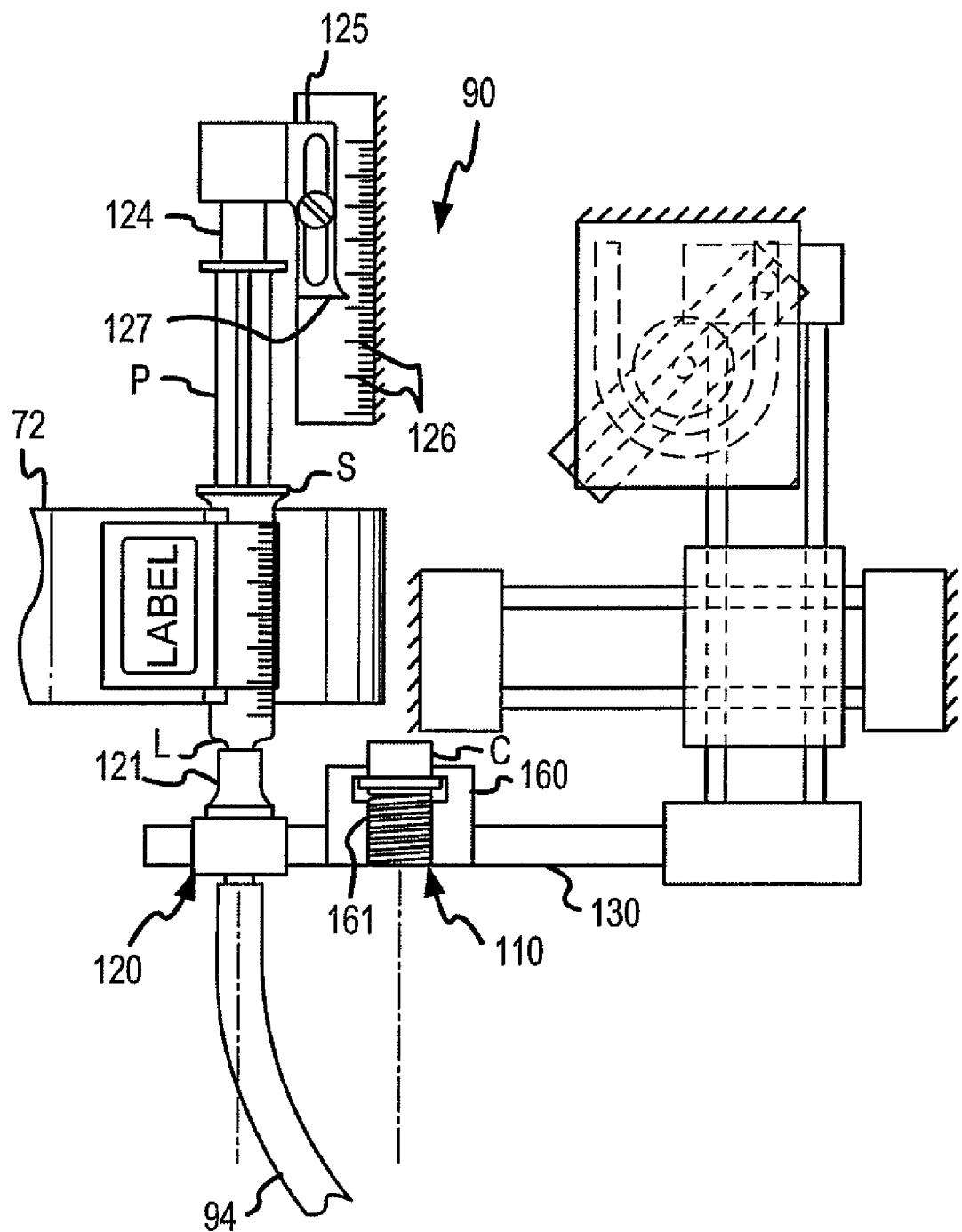

As best seen in FIG. 6d, the plunger P of the syringe S is pushed outwardly by the liquid medication that is pumped into the syringe S. When the syringe S has been filled with the desired volume of liquid medication, the flow of liquid medication into the syringe S is stopped. The flow can be measured and stopped in a variety of ways, such as flow meters, valves, known pump displacement, and the like, as would be within the knowledge and capabilities of persons skilled in the art once they understand the principles of this invention. However, a particularly novel and innovative way of controlling the fill volume according to this invention is to use a sensor 124 to detect when the plunger P has been pushed out to a predetermined extent that corresponds to the fill volume desired, as illustrated in FIG. 6d. A myriad of sensors could be used for this function, such as a capacitive proximity sensor, optical sensor, microswitch, and the like. Upon sensing the desired extension of the plunger P, a signal from the sensor 124 can be used to shut off the flow of liquid medication into the syringe S. A suitable signal control circuit, for example, a microprocessor and/or relay, (not shown) to shut off the pump 93 or to close some control valve (not shown) is well within the capabilities of persons skilled in the art once they understand the principles of this invention. As shown in FIG. 6d, the sensor 124 can be mounted on an adjustable base 125 with a scale 126 and pointer 127 to correlate adjustable physical position of the sensor with the desired fill volume.

When the desired fill volume has been reached and detected, as explained above, a signal from the sensor 124 is used to deactuate the pump 93. A preferred, albeit not essential, pump 93 is a peristaltic pump, such as, for example, a model 099 Repeater Pump, manufactured by Baxa Corporation, of Englewood, Colo., which can be reversed momentarily to take the fluid pressure off the tubing 94 and syringe S to minimize, if not prevent, dripping of the liquid medication when the nozzle 121 is detached from the luer L. Then, the motor 133 is actuated to rotate the cam lever 134 in the opposite direction, as indicated by the arrow 159 in FIG. 6e, to detach the nozzle 121 from the luer L of the syringe S and move the jaws 160 and cap C back into longitudinal alignment with the axis 123 of the syringe S for replacing the cap C on the syringe S. Specifically, as the cam lever 134 rotates, as shown by arrow 159, the cammed shuttle 130 moves back through the U-shaped pattern defined by the U-shaped cam slot 139. First, the slide shafts 142, 143 are extended as indicated by arrow 171 to detach the nozzle 121 from the luer L of syringe S. Then the cammed shuttle is moved in an arc as indicated by arrow 172 to align the cap C in jaws 160 with the longitudinal axis 123 of the syringe S. Finally, the slide shafts 142, 143 are retracted again, as indicated by arrow 173, to push the cap C back onto the syringe S. The cap handling apparatus 110 can be mounted by a spring-loaded slide (not shown) or some other yieldable, resilient structure, if desired, to ensure a uniform pressure application to the cap C as it is being pushed by the cammed shuttle 130 back onto the syringe S.

Figure 6E:
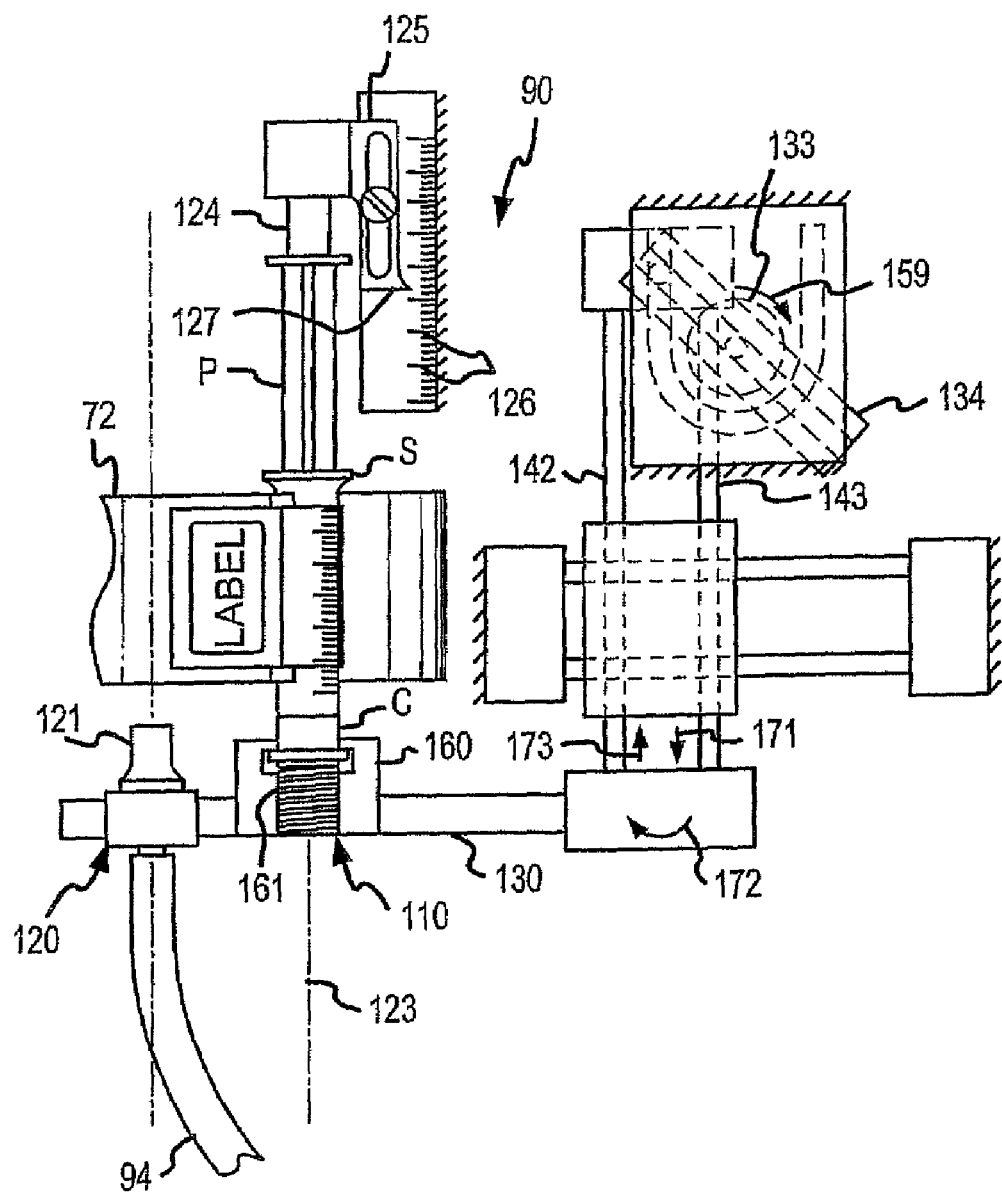

At this position, shown in FIG. 6e, the fill is completed, and the drum 72 can be rotated again to move the cap C out of the jaws 160 and to move the next syringe S in the sequence into the jaws 160 for a repeat of the cap removal, fill, and cap replacement sequence described above on the next syringe S in the drum 72. At the next position after the filling station 90, a sensor (not shown), such as an optical sensor, is used to determine if the cap C is placed correctly back on the syringe S. If it is not placed correctly, the apparatus is stopped and/or an alarm is sounded in response to a signal from the sensor indicating that the cap C is not replaced. After that cap-check position, the drum moves the syringe to a point where hold down or guide tracks end, thereby freeing the syringe S to drop out of the drum 72 and into a chute (not shown) that guides the labeled, filled, and recapped syringe S into the holding basket 115.

The control system (not shown) can utilize signals from the sensors to record number of syringes S filled, program the number of doses desired and automatically stop when that number of syringes S are filled, record the number of doses actually pumped, record the number of doses or syringes in the basket 115 and keep track of rejected labels or syringes. Other functions can also be provided.

Figure 7A:
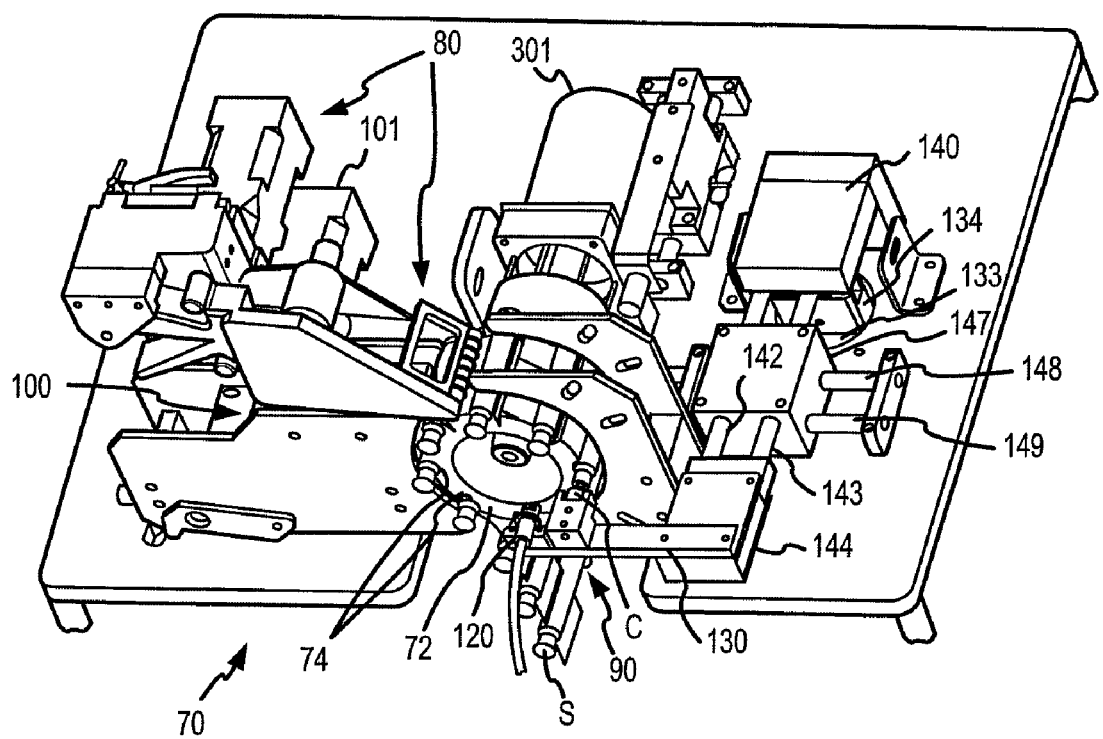
FIGS. 7a and 7b comprise isometric assembly and exploded views, respectively, of a labeling and filling apparatus of the embodiment corresponding with FIGS. 5 and 6a-e.
Figure 7B:
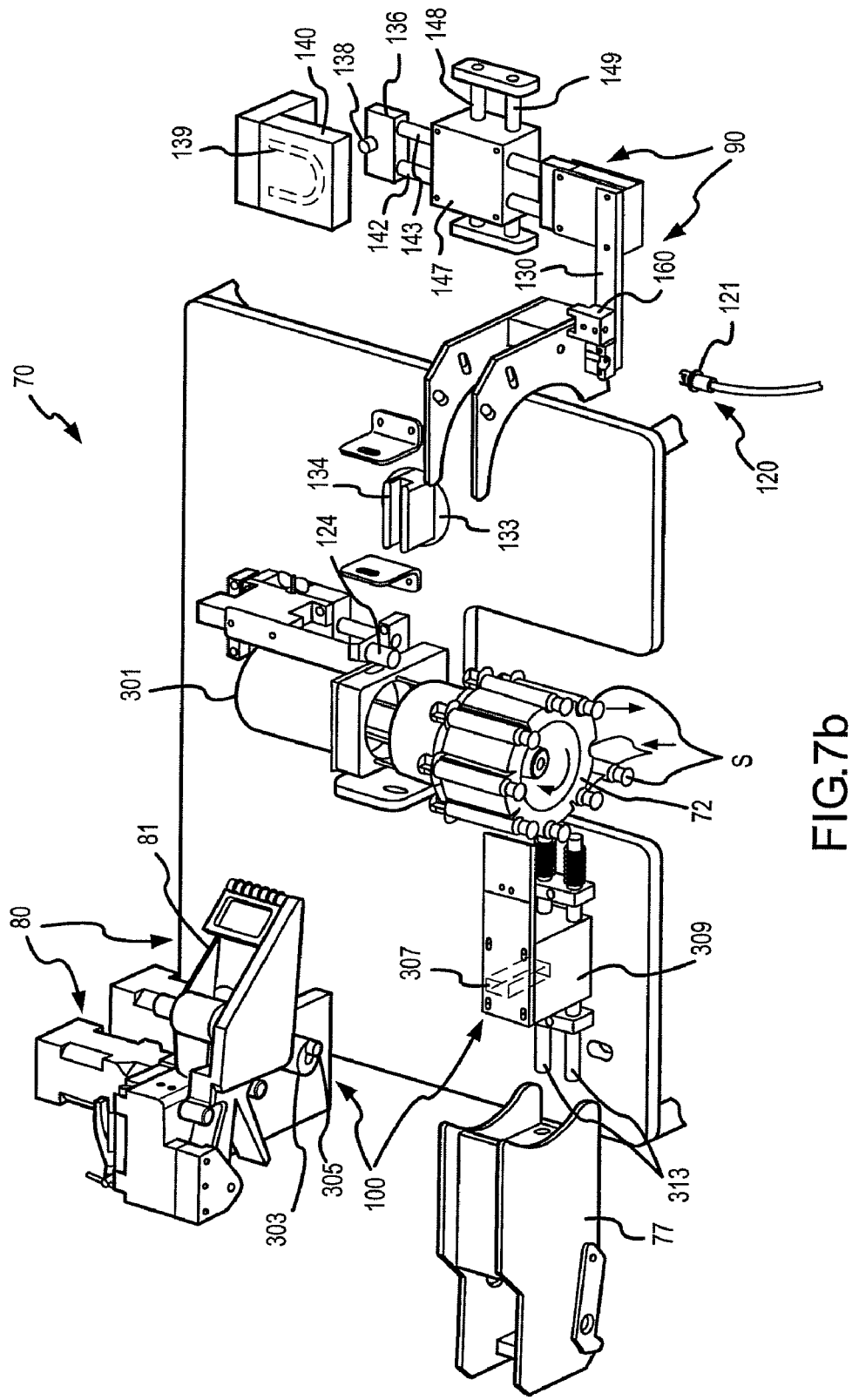

Referring now to FIGS. 7a and 7b, the labeling and filling apparatus embodiment of FIG. 5 and FIG. 6a-6e is further illustrated in a production implementation. Of note, the labeling and filling apparatus 70 is shown in a compact table top arrangement that may be readily positioned in a sterile environment, e.g. within a sterile area having an appropriate exhaust hood. As will be recognized, the apparatus 70 includes a cutting station 100, labeling station 80 and filling station 90.

The drum 72 may be driven in a clockwise direction by a step motor 301, wherein syringes S are positioned into the notches 74 for sequential feeding to the work stations 80, 90 and 100. At cutting station 100, an actuator 101 in the form of a stepper motor may be utilized. In particular, the actuator 101 may be controlled to turn a crank 303 having a cam follower 305 that is located in a slot 307 on a mount block 309 for cutting blade 102. The block 309 is supported on rails 313, wherein driven rotation of the crank 303 effects linear travel of the cutting blade 102 towards and away from the drum 72 and a belt 30 with syringes S carried thereby. The operation of actuator 101 may be timed in relation to the stepped movement of drum 72 so that belt 30 is cut into belt segments 10 of a consistent width by cutting blade 102.

At labeling station 80, the labeling device 81 may include a stepper motor (not illustrated) to which a shaft (not illustrated) is interconnected for driven eccentric motion. That is, upon actuation stepper motor may drive shaft through an arc from a first position to a second position. By way of example, the first position may be as illustrated in FIGS. 7a and 7b, wherein the labeling device 81 is located in a down position for label placement. Upon eccentric motion of the shaft to a second position, shaft will engage the labeling device 81 causing the cantilevered end thereof to cock upwards about a stationary shaft (not illustrated). As may be appreciated, the operation of stepper motor is timed in relation to the stepped movement of drum 72 to affect label placement on the belt segments 10 between adjacent syringes S.

Figure 8B:
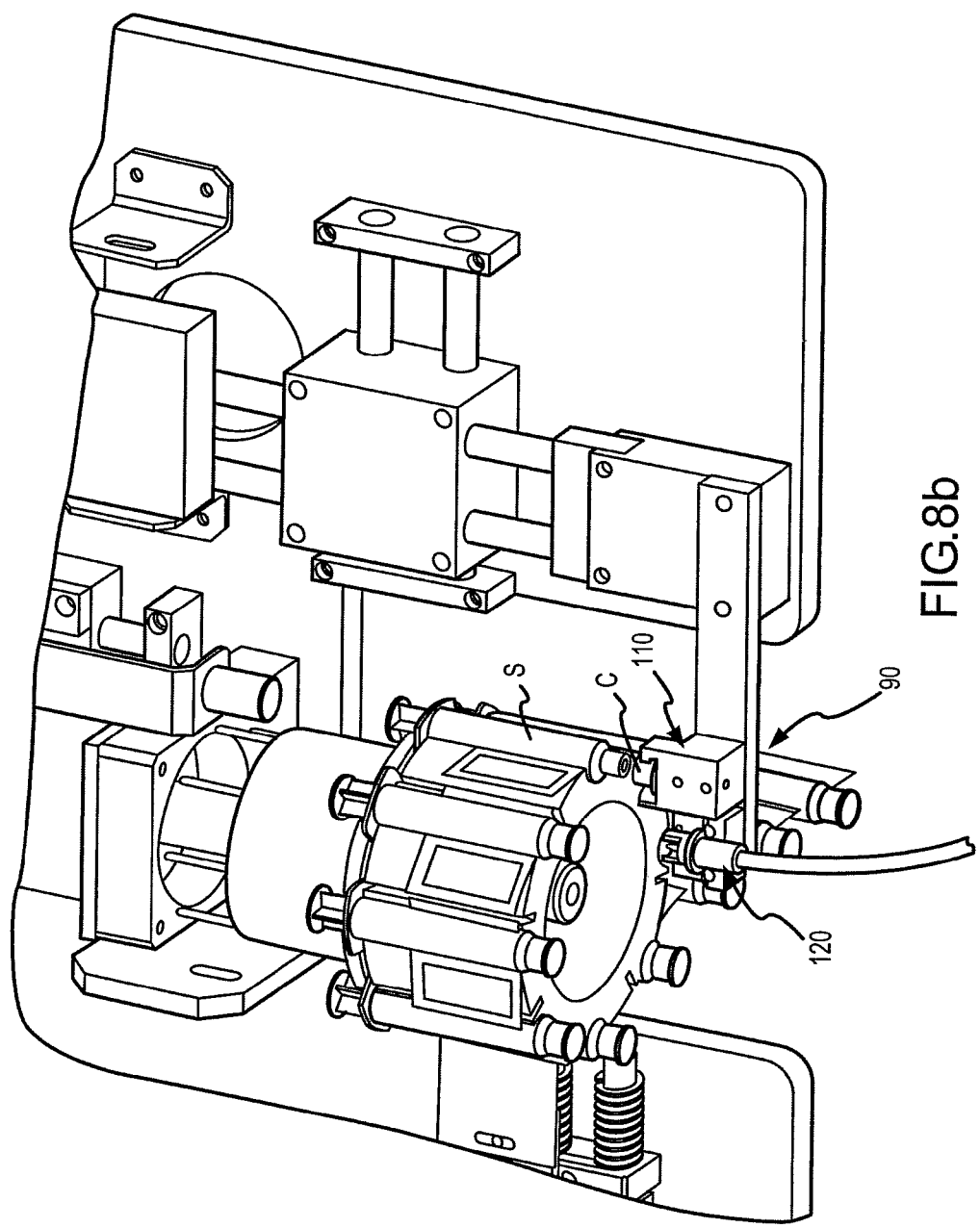

Referring now to FIGS. 8a-8d, operation of the filling station 80 shown in FIGS. 7a and 7b will be further described. In FIG. 8a a syringe S has advanced to the filling station 90 with a cap C inserted into cap handling apparatus 110. As illustrated, syringe S has an interconnected belt segment on flap 10 with a label 12 adhered thereto.

As next shown in FIG. 8b, it can be seen that filling station 90 has retracted away from drum 72 so as to remove cap C from the dispensing end of the syringe S. As previously noted, such retraction is achieved by activating stepper motor 133 to rotate cam lever 134, thereby causing driver block 136, slide shafts 142, 143, connecting block 144 and shuttle 130 to move along a first straight leg portion of U-shaped motion pattern.

Figure 8C:
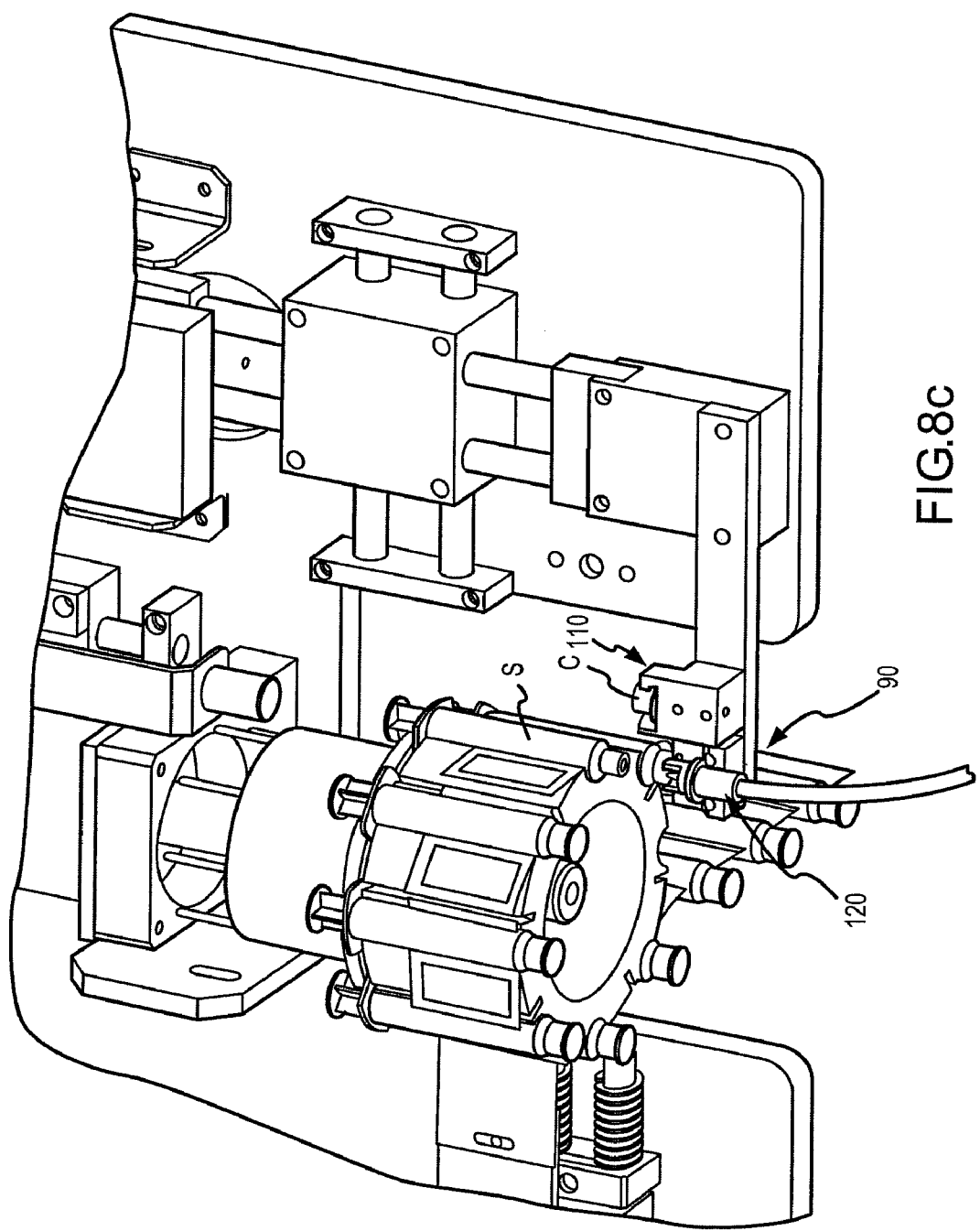

In the later regard, FIG. 8c shows the filling station 90 immediately after cam lever 134 has moved through the curved portion of the U-shaped motion pattern. In this position it can be seen that the nozzle 121 of the liquid dispensing apparatus 120 is aligned with the dispensing end of the syringe S. As such, and as seen in FIG. 8d, further movement of the filling station 90 along the second straight leg portion of the U-shaped motion pattern causes the liquid dispensing apparatus 120 to linearly advance towards syringe S, wherein the nozzle 121 engages and fluidly interconnects with the dispensing end of the syringe S. Upon reaching the FIG. 8d position, filling station 90 may be controlled so that fluid is injected through nozzle 121 into the syringe S. As further shown in FIG. 8d, fluid has filled the syringe S to displace the plunger P into contact with the sensor 124. At this point, a sensor signal is transmitted to terminate the filling of syringe S. Thereafter, stepper motor 133 may again rotate cam lever 134 through the U-shaped motion pattern to reposition cap C back onto the dispensing end of the syringe S.

As noted above, the filling and labeling apparatus 70 is only one embodiment of the present invention. Numerous other embodiments will be apparent to those skilled in the art. By way of example, reference is now made to FIGS. 9, 10 and 11a-11f, which illustrate an alternate embodiment.

Figure 9:
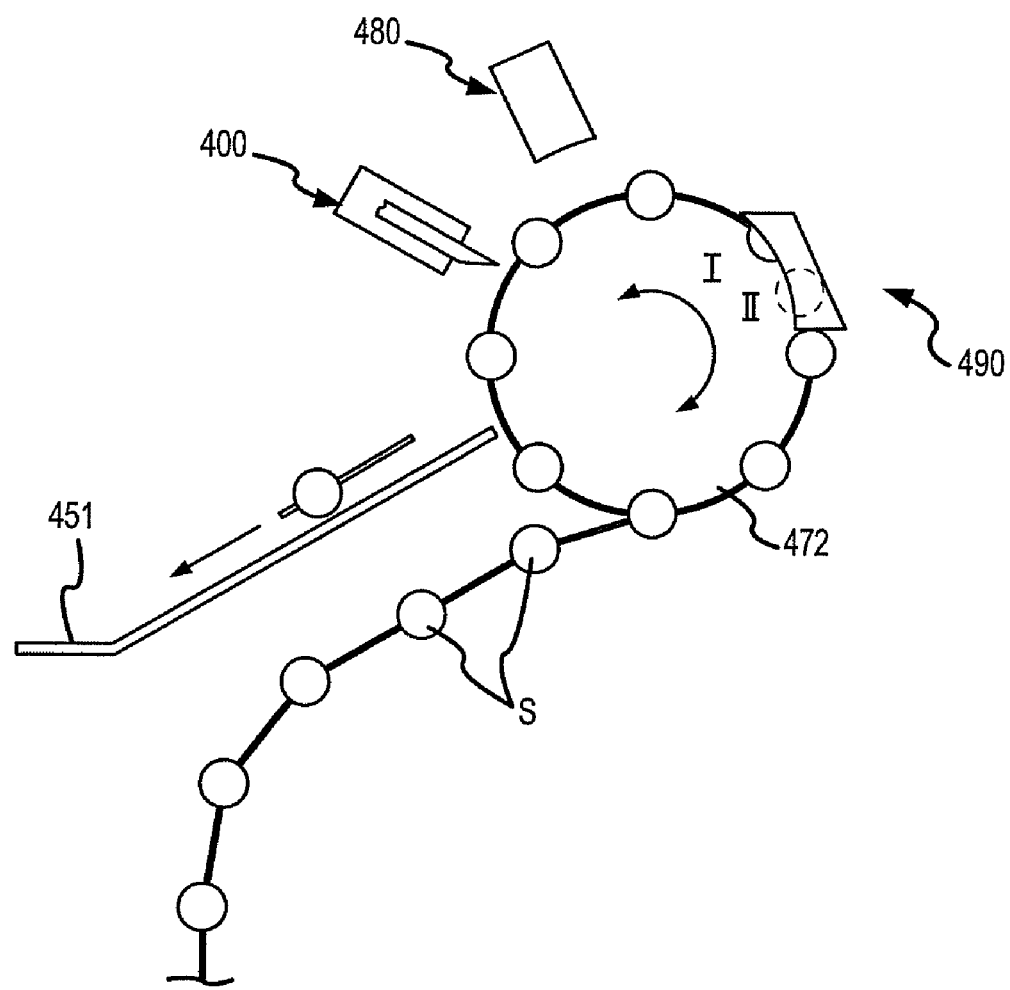
FIG. 9 is a schematic elevation view of a labeling and filling apparatus according to another embodiment of this invention.

In this embodiment a drum 472 is driven in a counter-clockwise direction, wherein a band 430 of syringes S pulled in series into the notches 474 for preparation operations. In the later regard, the band 430 is suspended from the drum 472 to facilitate aligned, side-by-side positioning of the syringes S in notches 474. As schematically shown in FIG. 9, the syringes S are sequentially advanced through filling station 490, labeling station 480 and cutting station 400. Thereafter, the separated syringes S may be directed into a container (not shown) via a chute 451. The operation of labeling station 480 and cutting station 400 may be analogous to the operations of the labeling station 80 and cutting station 100 described above in relation to FIG. 5 and FIGS. 6a-6b. In contrast to that embodiment, however, the embodiment shown in FIGS. 9, 10 and 11a-11h may implement a different approach at filling station 490.

Figure 10:
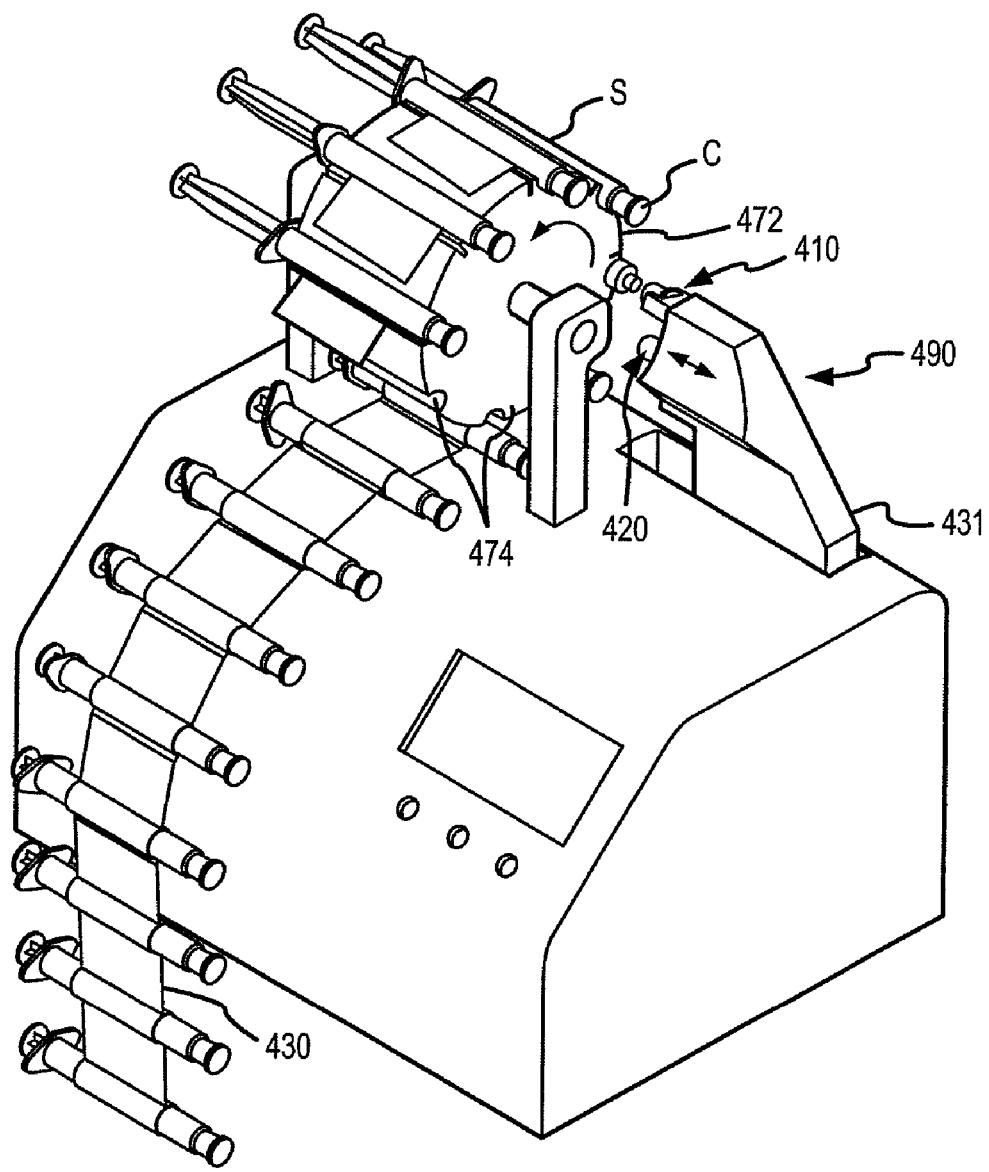
FIG. 10 is an isometric view of a syringe-filling station of the apparatus embodiment of FIG. 9.

In the modified operation shown in FIG. 9, a syringe is first positioned at location I for cap removal, then located at a second position II for filling, followed by location back at work location I for cap replacement. To facilitate an understanding of such approach, the labeling station 480 and cutting station 400 are not presented in FIG. 10. As best shown by FIG. 10, filling station 490 includes a cap handling apparatus 410 and liquid dispensing apparatus 420. As will be appreciated, liquid dispensing apparatus 420 is interconnectable to a reservoir (not shown) containing a fluid for filling syringes S. Of note, both the cap handling apparatus 410 and liquid dispensing apparatus 420 are mounted on a common support member 431. Support member 431 may be interconnected to a stepper motor (not shown) acutatable to affect linear travel of the cap handling apparatus 410 and liquid dispensing apparatus 420 towards and away from the drum 472. Such linear travel, together with the rotation of drum 472 are the only required motions for cap removal, filling and cap replacement. Such operations will now be further described with reference to FIGS. 11a-11h.

FIGS. 11a-11h are flat, diagrammatic views of filling station 490 from a rearward perspective relative to the isometric front view shown in FIG. 10. Before proceeding, it should be noted that the filling station 490 shown in FIGS. 11a-11h further includes a syringe flange retention track 492 and a plunger flange retention member 494. As will be further described, the plunger flange retention number 494 is selectively retractable relative to retention track 492 so that fluid may be drawn from liquid dispensing apparatus 420 to fill syringes S. In this regard, liquid dispensing apparatus 420 may include a valve to control the passage/stoppage of fluid therethrough. By way of example, such valve may comprise an actuatable roller.

Figure 11A:
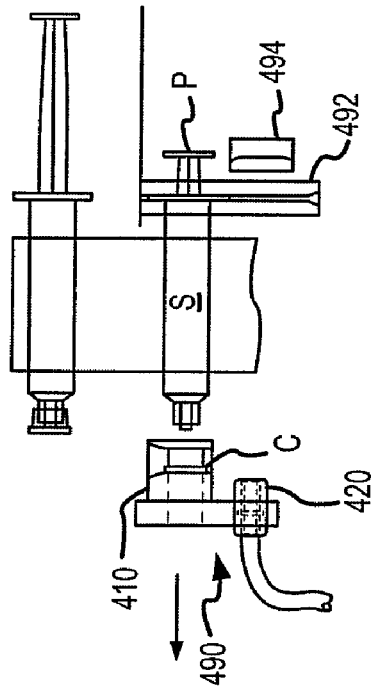
FIGS. 11a-11h are flat, diagrammatic views of syringe handling operations at the filling-station of the apparatus embodiment of FIGS. 9 and 10.
Figure 11B:
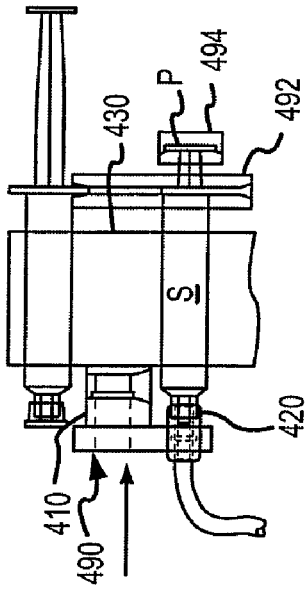

With particular reference to FIG. 11a, a syringe S is shown in the first location I shown in FIG. 9 wherein cap C has been inserted in the cap handling apparatus 410 for retention thereby. Concomitantly, a flange on syringe S has been inserted and advanced within the retention track 492. Next, and as shown in FIG. 11b, cap handling apparatus 410 has been retracted from the syringe S with cap C retained thereby. As will be appreciated, such retraction may be affected via linear driven travel of the support member 431 shown in FIG. 10.

Figure 11C:
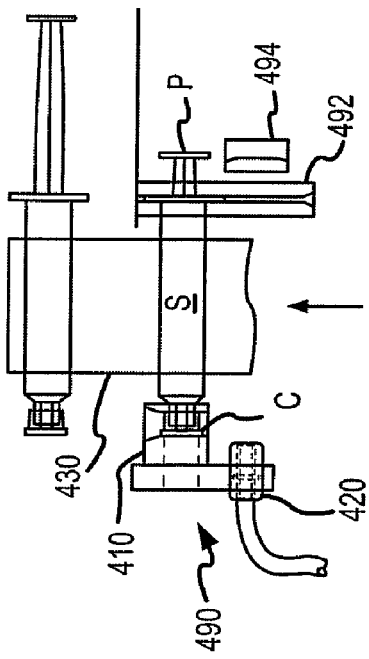
Figure 11D:
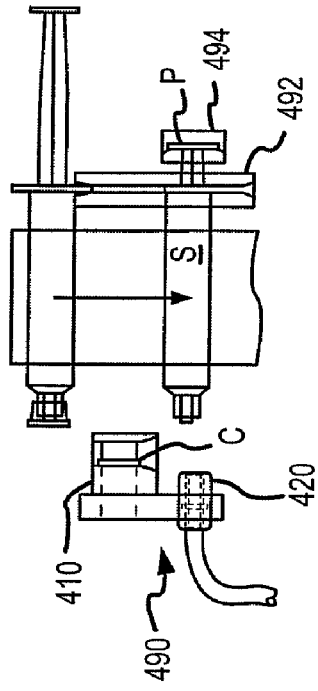

FIG. 11c shows the syringe S moved to the location II shown in FIG. 9. More particularly, drum 472 may be rotated clockwise to affect such positioning, wherein the liquid dispensing apparatus 420 is aligned with the dispensing end of the syringe S. Then, liquid dispensing apparatus 420 may be advanced into engagement with the dispensing end of syringe S as shown in FIG. 11d. Again, such linear travel may be affected via movement of support member 431. Of note, both FIGS. 11c and 11d show the plunger P being positioned in the retention member 494.

Figure 11E:
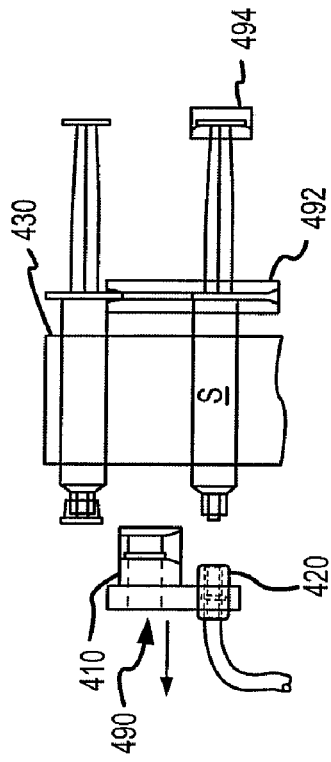
Figure 11F:
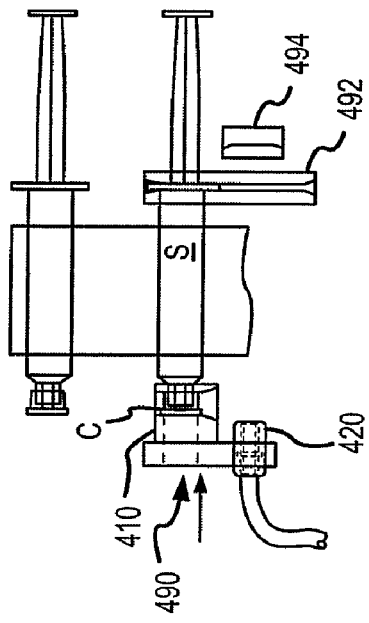

In this regard, and referring now to FIG. 11e, retention member 494 may be provided for driven retraction away from syringe S (e.g. via an unshown stepper motor), with the valve of liquid dispensing apparatus 420 opened so as to draw fluid through liquid dispensing apparatus 420 into the syringe S. As may be appreciated, the amount, or length, of retraction of retention member 494 may be precisely controlled to achieve a preset filling volume. When the desired volume has been reached, the valve of liquid dispensing apparatus 420 may be closed. Where an actuatable roller is utilized, the roller may be positioned to pinch off a fluid conduit to back up the fluid a desired amount, thereby bringing the fluid pressure slightly below atmospheric pressure. After filling, the liquid dispensing apparatus 420 may be withdrawn from the dispensing end of the syringe S as shown in FIG. 11f. Again, such linear travel may be affected by controlled retraction of the support member 431.

Figure 11G:
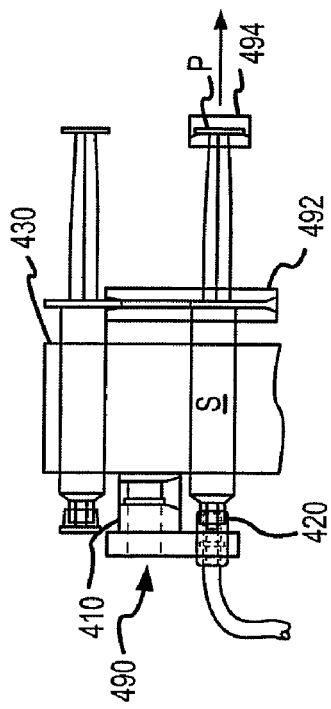
Figure 11H:
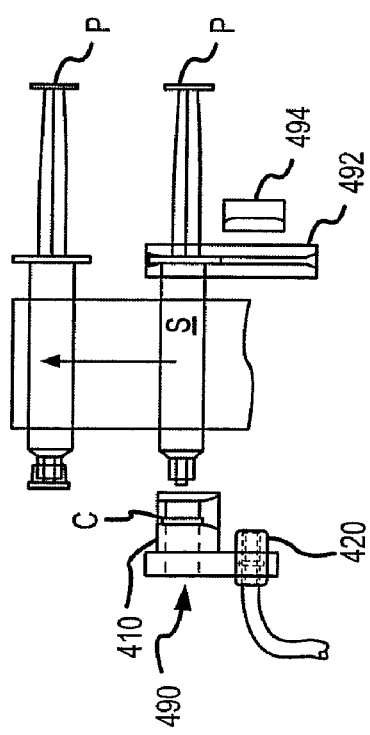
Figure 12A:
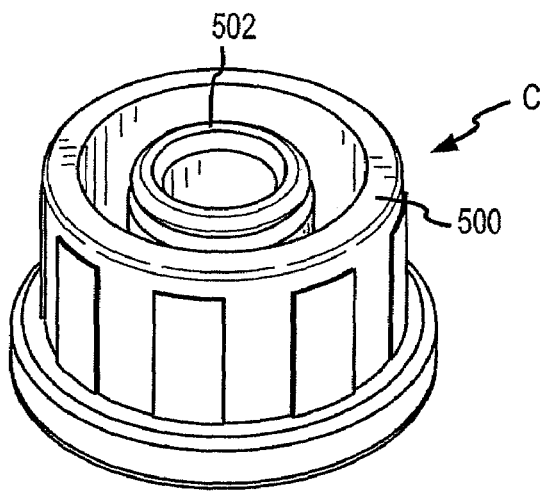
FIGS. 12a-12c are isometric, end and cross-sectional views of a syringe cap employable in one embodiment of the syringe shown in FIG. 1.
Figure 12B:
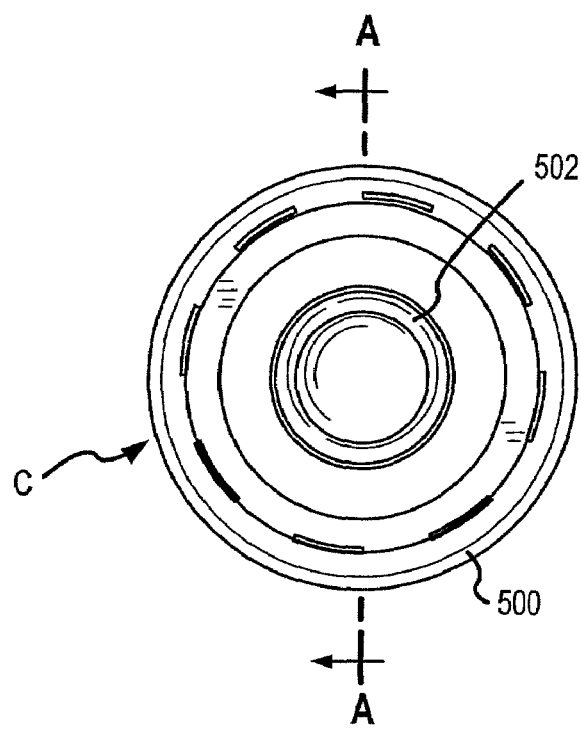
Figure 12C:
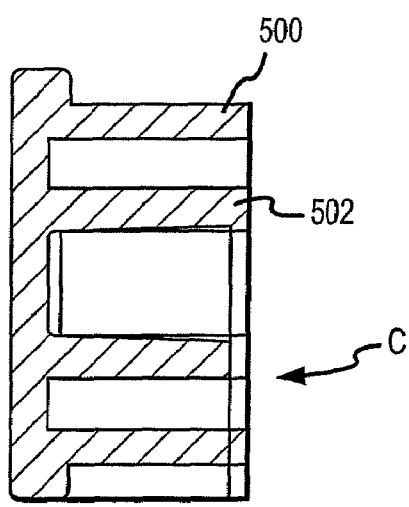
Figure 13A:
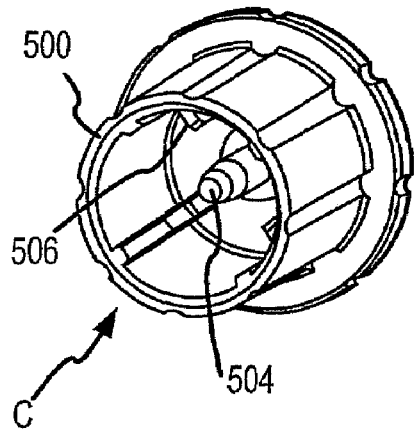
FIGS. 13a-13c are isometric, end and cross-sectional views of a syringe cap employable in another embodiment of the syringe shown in FIG. 1.
Figure 13B:
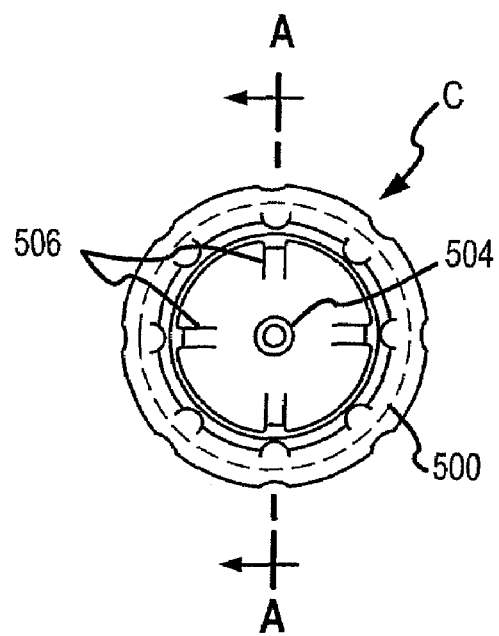
Figure 13C:
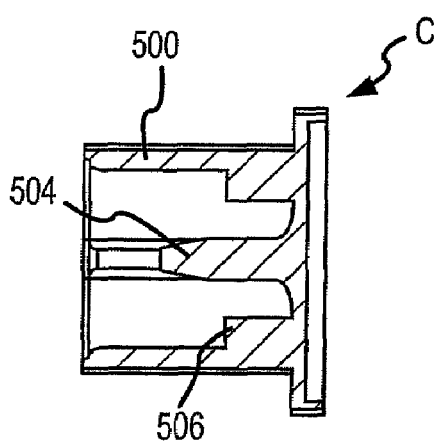

Thereafter, syringe S may return to location I via counterclockwise rotation of drum 472, as shown in FIG. 11g. Finally, cap C may be replaced onto the dispensing end of the syringe S via advancement of the cap handling apparatus 410 on support member 431. The syringe S may then be advanced for further operations at the labeling station 480 and cutting station 400 shown in FIG. 9.

The foregoing description is considered as illustrative only of the principles of the invention. Furthermore, since numerous modifications and changes will readily occur to those skilled in the art, it is not desired limit the invention to the exact construction and process shown and described above. Accordingly, resort may be made to all suitable modifications and equivalents that fall within a scope of the invention as defined by the claims which follow. The words "comprise," "comprises," "comprising," "include," "including," and "includes" when used in this specification are intended to specify the presence of stated features, integers, components, or steps, but they do not preclude the presence or addition of one or more other features, integers, components, steps, or groups thereof.

What is claimed is:

1. A method for handling a plurality of syringe bodies, comprising:
    interconnecting a belt to a plurality of a syringe bodies in a predetermined orientation, wherein each of said plurality of interconnected syringe bodies comprises a barrel, a plunger slidably disposed in one end of the barrel and a cap disposed on another end of the barrel, wherein for each of said plurality of syringe bodies, a contained volume is defined within said barrel between the plunger and the cap, wherein said interconnecting includes attaching opposing layers to define said belt, and wherein said opposing layers are adjoined in face-to-face relation between adjacent ones of said plurality of syringe bodies and wrapped about opposing sides of the barrels of each of said plurality of syringe bodies; and
    packaging said plurality of interconnected syringe bodies in a container.

2. A method as recited in claim 1, further comprising:
    sterilizing said plurality of interconnected syringe bodies after said packaging step.

3. A method as recited in claim 1, further comprising:
    positioning said plurality of syringe bodies in said predetermined orientation prior to said interconnecting step.

4. A method as recited in claim 1, wherein said belt is of a pliable construction.

5. A method as recited in claim 1, wherein said interconnecting step comprises:
    attaching at least one continuous layer of a pliable material between and about at least a portion of each of said plurality of syringe bodies.

6. A method as recited in claim 5, wherein said at least one continuous layer is substantially transparent.

7. A method as recited in claim 1, wherein at least a first one of said opposing layers is opaque.

8. A method as recited in claim 7, wherein a second one of said opposing layers is substantially transparent.

9. A method as recited in claim 8, wherein the barrel of each of said plurality of syringe bodies comprises graduated volume indications along a length thereof, wherein at least a portion of said graduated volume indications are visible through said substantially transparent second one of said opposing layers.

10. A method as recited in claim 1, wherein said opposing layers are substantially transparent.

11. A method as recited in claim 1, wherein said packaging step comprises:
    fan folding said plurality of interconnected syringe bodies.

12. A method for handling and labeling a plurality of syringe bodies, comprising:
    interconnecting a belt to a plurality of a syringe bodies in a predetermined orientation, wherein each of said plurality of interconnected syringe bodies comprises a barrel, a plunger slidably disposed in one end of the barrel and a cap disposed on another end of the barrel, wherein for each of said plurality of syringe bodies a contained volume is defined within said barrel between the plunger and the cap, wherein said interconnecting includes attaching opposing layers to define said belt, and wherein said opposing layers are adjoined in face-to-face relation between adjacent ones of said plurality of syringe bodies and wrapped about opposing sides of the barrels of each of said plurality of syringe bodies;
    packaging said plurality of interconnected syringe bodies in a container;
    unpackaging said plurality of interconnected syringe bodies after said packaging step; and
    placing contents-related information on belt segments between and in corresponding relation to each of said plurality of syringe bodies.

13. A method as recited in claim 12, further comprising:
    sterilizing said plurality of interconnected syringe bodies after said packaging step and prior to said unpackaging step.

14. A method as recited in claim 12, further comprising:
    positioning said plurality of syringe bodies in said predetermined orientation prior to said interconnecting step.

15. A method as recited in claim 12, further comprising:
    first completing said interconnecting and packaging steps at a production location; and
    second completing said unpackaging and placing steps at another location.

16. A method as recited in claim 15, further comprising:
    shipping said container from said production location to said another location.

17. A method as recited in claim 15, further comprising:
    sterilizing said plurality of interconnected syringe bodies at said production location.

18. A method as recited in claim 17, wherein said sterilizing step is completed after said packaging step and prior to said unpackaging step.

19. A method as recited in claim 12, wherein said interconnecting step comprises:
attaching at least one continuous layer of a pliable material between and about at least a portion of each of said plurality of syringe bodies.

20. A method as recited in claim 19, wherein said at least one continuous layer is substantially transparent.

21. A method as recited in claim 1, wherein at least a first one of said opposing layers is opaque.

22. A method as recited in claim 21, wherein a second one of said opposing layers is substantially transparent.

23. A method as recited in claim 22, wherein the barrel of each of said plurality of syringe bodies comprises graduated volume indications along a length thereof, wherein at least a portion of said graduated volume indications are visible through said substantially transparent second one of said opposing layers.

24. A method as recited in claim 1, wherein said opposing layers are substantially transparent.

25. A method as recited in claim 12, further comprising:
separating said belt between each of said plurality of syringe bodies to define an interconnected flap on each of said plurality of syringe bodies, wherein each interconnected flap includes a different corresponding one of said belt segments.

26. A method as recited in claim 12, wherein said belt is of a pliable construction.

* * * * *

UNITED STATES PATENT AND TRADEMARK OFFICE
CERTIFICATE OF CORRECTION

| | | |
|---|---|---|
| PATENT NO. | : 7,469,518 B2 | Page 1 of 1 |
| APPLICATION NO. | : 11/427740 | |
| DATED | : December 30, 2008 | |
| INVENTOR(S) | : Baldwin | |

It is certified that error appears in the above-identified patent and that said Letters Patent is hereby corrected as shown below:

Column 18, line 36 claim 12, delete "adioined", and insert therefor --adjoined--.

Signed and Sealed this

Seventeenth Day of February, 2009

JOHN DOLL
*Acting Director of the United States Patent and Trademark Office*